United States Patent
Ishibuchi et al.

(10) Patent No.: US 7,105,567 B2
(45) Date of Patent: Sep. 12, 2006

(54) 3-SUBSTITUTED UREA DERIVATIVES AND MEDICINAL USE THEREOF

(75) Inventors: Seigo Ishibuchi, Tokyo (JP); Hiroshi Sumichika, Tokyo (JP); Katsuhiko Itoh, Saitama (JP); Yoichi Naka, Nakatsu (JP)

(73) Assignee: Mitsubishi Pharma Corporation, Osaka (JP)

( * ) Notice: Subject to any disclaimer, the term of this patent is extended or adjusted under 35 U.S.C. 154(b) by 31 days.

(21) Appl. No.: 10/343,961

(22) PCT Filed: Aug. 10, 2001

(86) PCT No.: PCT/JP01/06902
§ 371 (c)(1),
(2), (4) Date: Feb. 5, 2003

(87) PCT Pub. No.: WO02/14265
PCT Pub. Date: Feb. 21, 2002

(65) Prior Publication Data
US 2003/0207939 A1    Nov. 6, 2003

(30) Foreign Application Priority Data
Aug. 10, 2000 (JP) ............. 2000-243290

(51) Int. Cl.
  *A61K 31/36*  (2006.01)
  *A61K 31/17*  (2006.01)
  *C07D 317/44*  (2006.01)
  *C07C 275/28*  (2006.01)
  *C07C 275/30*  (2006.01)

(52) U.S. Cl. ............ 514/466; 514/596; 514/597; 514/598; 564/48; 564/50; 564/51; 564/52; 564/53; 564/54; 549/439

(58) Field of Classification Search ......... 564/48, 564/50, 51, 52, 53, 54; 514/596, 597, 598
See application file for complete search history.

(56) References Cited

U.S. PATENT DOCUMENTS 4,405,644 A * 9/1983 Kabbe et al. ............. 514/522
4,868,210 A * 9/1989 Trivedi ................... 514/539
5,063,247 A * 11/1991 Sekiya et al. ............ 514/585

FOREIGN PATENT DOCUMENTS

| EP | 0 512 570 | 11/1992 |
| EP | 512570 | 11/1992 |
| GB | 930918 | * 7/1963 |
| JP | 10-182648 | 7/1998 |
| WO | WO 94/07815 | 4/1994 |
| WO | 98/07418 | 2/1998 |
| WO | WO 99/00406 | 1/1999 |

OTHER PUBLICATIONS

C. Gerard et al., "C5a Anaphylatoxin and its Seven Transmembrane-Segment Receptor", Annu. Rev. Immunol., vol. 12, pp. 775-808, 1994.
J. Ember et al., "Complement Factors and Their Receptors", Immunopharmacology, vol. 38, pp. 3-15, 1997.
T. Pellas et al., "C5a Receptor Antagonists", Current Pharmaceutical Design, vol. 5, pp. 737-755, 1999.
A. Wong et al., "Development of C5a Receptor Antagonists", IDrugs, vol. 2, pp. 686-693, 1999.
Lanza et al., "Substituted 4, 6-diaminoquinolines as inhibitors of C5a receptor binding", Journal of Medicinal Chemistry, vol. 35, No. 2, pp. 252-258, 1992.

* cited by examiner

*Primary Examiner*—Peter G. O'Sullivan
(74) *Attorney, Agent, or Firm*—Wenderoth, Lind & Ponack, L.L.P.

(57) ABSTRACT

The present invention relates to a urea derivative of the formula (1)

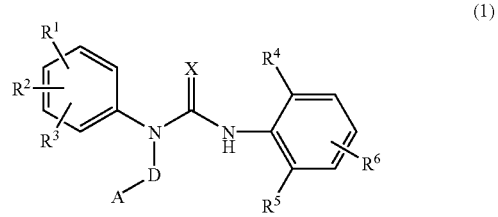

(1)

wherein each symbol is as described in the specification, a pharmaceutically acceptable salt thereof and pharmaceutical use thereof. The compound of the present invention has a C5a receptor antagonistic action and is useful as an agent for the prophylaxis or treatment of diseases or syndromes due to inflammation caused by C5a [e.g., autoimmune diseases such as rheumatism, systemic lupus erythematosus and the like, sepsis, adult respiratory distress syndrome, chronic obstructive pulmonary disease, allergic diseases such as asthma and the like, atherosclerosis, cardiac infarction, brain infarction, psoriasis, Alzheimer's disease and serious organ injury (e.g., pneumonia, nephritis, hepatitis, pancreatitis and the like) due to activation of leukocytes caused by ischemia, trauma, burn, surgical invasion and the like]. In addition, it is useful as an agent for the prophylaxis or treatment of infectious diseases caused by bacteria or virus that invades via a C5a receptor.

14 Claims, No Drawings

3-SUBSTITUTED UREA DERIVATIVES AND MEDICINAL USE THEREOF

This application is a U.S. national stage of International Application No. PCT/JP01/06902 filed Aug. 10, 2001.

TECHNICAL FIELD

The present invention relates to a urea derivative showing a C5a receptor antagonistic action and useful for the prophylaxis or treatment of autoimmune diseases such as rheumatism and systemic lupus erythematosus and the like, sepsis, adult respiratory distress syndrome, chronic obstructive pulmonary disease, allergic diseases such as asthma and the like, atherosclerosis, cardiac infarction, brain infarction, psoriasis, Alzheimer's disease or serious organ injuries (e.g., pneumonia, nephritis, hepatitis and pancreatitis and the like) due to activation of leukocytes caused by ischemia, trauma, burn, surgical invasion and the like, a pharmaceutically acceptable salt thereof and pharmaceutical use thereof.

BACKGROUND ART

When the complement system is activated, the protein of the complement system is enzymolysed and fragments having various physiological activities are produced. One of the fragments, complement component C5a, is a glycoprotein having a molecular weight of about 11,000, consists of 74 amino acids and has a strong inflammation inducing action. C5a has a broad range of actions such as smooth muscle contraction, promotion of blood vessel permeability, migration of leukocyte, degranulation of leukocyte, production of reactive oxygen species, reinforcement of antibody production, induction of production of cytokine, TNF (tumor necrosis factor), leukotriene and the like, and the like, and is said to be a causative substance of diseases such as autoimmune diseases (e.g., rheumatism and systemic lupus erythematosus and the like), sepsis, adult respiratory distress syndrome, chronic obstructive pulmonary disease, allergic diseases (e.g., asthma and the like), atherosclerosis, cardiac infarction, brain infarction, psoriasis, Alzheimer's disease, serious organ injuries (e.g., pneumonia, nephritis, hepatitis, pancreatitis and the like) due to activation of leukocytes caused by ischemia, trauma, burn, surgical invasion and the like, and the like [Annu. Rev. Immunol., vol. 12, pp. 775–808 (1994), Immunopharmacology, vol. 38, pp. 3–15 (1997), Curr. Pharm. Des., vol. 5, pp. 737–755 (1999) and IDrugs, vol. 2, pp. 686–693 (1999)].

Accordingly, a non-peptide small molecular compound having a C5a receptor antagonistic action is expected as a novel non-steroid type antiinflammatory drug. In addition, it can be expected as a prophylactic or therapeutic drug of infectious diseases caused by bacteria or virus that invades via a C5a receptor.

As regards the C5a antagonist, for example, the following patent applications have been published. JP-A-10-182648 discloses TAN-2474 related compounds having a C5a antagonistic action. In addition, the specification of WO94/07815 discloses peptide derivatives having a C5a receptor antagonistic action, the specification of WO99/00406 discloses cyclic peptide derivatives having a C5a receptor antagonistic action.

Heretofore, however, a pharmaceutical drug, that prevents or treats diseases or syndromes due to the inflammation caused by C5a by inhibiting the action of C5a, has not been developed.

DISCLOSURE OF THE INVENTION

In view of the above-mentioned situation, the present inventors have conducted intensive studies with the aim of finding a non-peptide compound having a C5a receptor antagonistic action. As a result, they have found that a urea derivative according to the present invention shows a C5a receptor antagonistic action, which resulted in the completion of the present invention.

Accordingly, the present invention provides the following.

(1) A urea derivative of the formula (1)

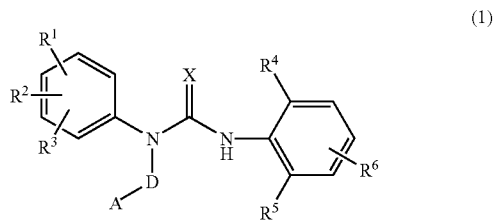

wherein
$R^1$, $R^2$ and $R^3$ are the same or different and each is hydrogen, alkyl optionally having a substituent, cycloalkyl optionally having a substituent, alkenyl optionally having a substituent, alkynyl optionally having a substituent, hydroxy, alkoxy optionally having a substituent, mercapto, alkylthio optionally having a substituent, halogen, nitro, nitrile, amino, alkylamino, cyclic amino, alkylsulfonyl, carbamoyl, acylamino, sulfamoyl, acyl, carboxy, alkoxycarbonyl, aryl optionally having a substituent or heteroaryl optionally having a substituent, D is a bond or alkylene optionally having a substituent, A is alkyl optionally having a substituent, cycloalkyl optionally having a substituent, aryl optionally having a substituent or heteroaryl optionally having a substituent, $R^4$ and $R^5$ are the same or different and each is hydrogen, alkyl optionally having a substituent, alkoxy optionally having a substituent, hydroxy or halogen, $R^6$ is hydrogen, alkyl optionally having a substituent, alkoxy optionally having a substituent, hydroxy or halogen, and X is oxygen atom or sulfur atom, or a pharmaceutically acceptable salt thereof.

(2) The urea derivative of the aforementioned (1), wherein D of the formula (1) is alkylene optionally having a substituent and A is aryl optionally having a substituent or heteroaryl optionally having a substituent, or a pharmaceutically acceptable salt thereof.

(3) The urea derivative of the aforementioned (1) or (2), wherein $R^1$, $R^2$ and $R^3$ of the formula (1) are the same or different and each is hydrogen or alkyl having 2 to 4 carbon atoms, or a pharmaceutically acceptable salt thereof.

(4) The urea derivative of any of the aforementioned (1) to (3), wherein $R^4$ and $R^5$ of the formula (1) are the same or different and each is alkyl, alkoxy or halogen, or a pharmaceutically acceptable salt thereof.

(5) The urea derivative of any of the aforementioned (1) to (4), which is a compound selected from N-benzyl-N'-(2,6-dimethylphenyl)-N-(4-octylphenyl)urea, N'-(2,6-diisopropylphenyl)-N-[(4-methoxyphenyl)methyl]-N-(4-octylphenyl)urea, N'-(2,6-diisopropylphenyl)-N-[(4-dimethylaminophenyl)methyl]-N-(4-octylphenyl)urea, N-(4-butylphenyl)-N'-(2,6-diisopropylphenyl)-N-[(4-dimethylaminophenyl)methyl]urea,
N'-(2,6-diisopropylphenyl)-N-[(4-dimethylaminophenyl)methyl]-N-(4-methoxyphenyl)urea,
N'-(2,6-diisopropylphenyl)-N-[(4-dimethylaminophenyl)methyl]-N-(4-ethylphenyl)urea,
N'-(2,6-diisopropylphenyl)-N-[(4-dimethylaminophenyl)methyl]-N-(4-propylphenyl)urea,
N'-(2,6-diisopropylphenyl)-N-[(4-dimethylaminophenyl)methyl]-N-(4-isopropylphenyl)urea,
N'-(2,6-diisopropylphenyl)-N-[(4-dimethylaminophenyl)methyl]-N-(4-ethoxyphenyl)urea,
N'-(2,6-diisopropylphenyl)-N-(4-isopropylphenyl)-N-[(4-isopropylphenyl)methyl]urea,
N-butyl-N'-(2,6-diisopropylphenyl)-N-(4-isopropylphenyl)urea,
N-(3,4-dichlorophenylmethyl)-N'-(2,6-diisopropylphenyl)-N-(4-isopropylphenyl)urea,
N'-(2,6-diisopropylphenyl)-N-[(2,4-dimethoxyphenyl)methyl]-N-(4-isopropylphenyl)urea,
N'-(2,6-diisopropylphenyl)-N-[(4-dimethylaminophenyl)methyl]-N-(2,4-dimethylphenyl)urea,
N-(benzo[d]1,3-dioxolen-5-ylmethyl)-N'-(2,6-diisopropylphenyl)-N-(4-isopropylphenyl)urea,
N'-(2,6-diisopropylphenyl)-N-[(2,4-dimethylphenyl)methyl]-N-(4-isopropylphenyl)urea,
N'-(2,6-diisopropylphenyl)-N-[(4-fluorophenyl)methyl]-N-(4-isopropylphenyl)urea,
N-[(4-chlorophenyl)methyl]-N'-(2,6-diisopropylphenyl)-N-(4-isopropylphenyl)urea,
N-[(4-bromophenyl)methyl]-N'-(2,6-diisopropylphenyl)-N-(4-isopropylphenyl)urea,
N'-(2,6-diisopropylphenyl)-N-(4-isopropylphenyl)-N-[(4-trifluoromethylphenyl)methyl]urea,
N-[(2,4-dichlorophenyl)methyl]-N'-(2,6-diisopropylphenyl)-N-(4-isopropylphenyl)urea,
N'-(2,6-diisopropylphenyl)-N-[(4-hydroxyphenyl)methyl]-N-(4-isopropylphenyl)urea and
N'-(2,6-diisopropylphenyl)-N-(4-isopropylphenyl)-N-[(4-methylthiophenyl)methyl]urea, or a pharmaceutically acceptable salt thereof.

The present invention further relates to the following pharmaceutical compositions.
(6) A pharmaceutical composition comprising the urea derivative of any of the aforementioned (1) to (5) or a pharmaceutically acceptable salt thereof, and a pharmaceutically acceptable additive.
(7) A prophylactic or therapeutic drug of a disease, in which C5a is involved, which comprises the urea derivative of any of the aforementioned (1) to (5) or a pharmaceutically acceptable salt thereof as an active ingredient.
(8) The prophylactic or therapeutic drug of the aforementioned (7), wherein the disease, in which C5a is involved, is an autoimmune disease, sepsis, adult respiratory distress syndrome, chronic obstructive pulmonary disease, an allergic disease such as asthma and the like, atherosclerosis, cardiac infarction, brain infarction, psoriasis, Alzheimer's disease, ischemia, trauma, burn or serious organ injury.
(9) A C5a receptor antagonist comprising the urea derivative of any of the aforementioned (1) to (5) or a pharmaceutically acceptable salt thereof as an active ingredient.
(10) The C5a receptor antagonist of the aforementioned (9), which is a prophylactic or therapeutic drug of an infectious disease caused by bacteria or virus that invades via the C5a receptor.
(11) The C5a receptor antagonist of the aforementioned (9), which is used in combination with an agent for the prophylaxis or treatment of an autoimmune disease, sepsis, adult respiratory distress syndrome, chronic obstructive pulmonary disease, an allergic disease such as asthma and the like, atherosclerosis, cardiac infarction, brain infarction, psoriasis, Alzheimer's disease, ischemia, trauma, burn or serious organ injury.
(12) A combination drug with an agent for the prophylaxis or treatment of an autoimmune disease, sepsis, adult respiratory distress syndrome, chronic obstructive pulmonary disease, an allergic disease such as asthma and the like, atherosclerosis, cardiac infarction, brain infarction, psoriasis, Alzheimer's disease, ischemia, trauma, burn or serious organ injury, which comprises the urea derivative of any of the aforementioned (1) to (5) or a pharmaceutically acceptable salt thereof as an active ingredient.

DETAILED DESCRIPTION OF THE INVENTION

The compound of the present invention is characterized in that it has a substituent on the nitrogen atom at the 1-position of N-substituted phenyl-N'-substituted phenyl urea. Due to this chemical characteristic, a C5a receptor antagonistic action is acquired. Some of the terms used in the present specification are defined as follows.

The "C5a receptor antagonistic drug" and "C5a receptor antagonist" are substances that inhibit the bond between a C5a receptor and "substances that bind to a C5a receptor".

The "substances that bind to a C5a receptor" means C5a, a hydrolysates of C5a (e.g., C5a desArg wherein the carboxy terminal arginine of C5a has been deleted), and substances having affinity for known or unknown C5a receptor.

The "C5a receptor antagonistic action" means an action that inhibits a reaction that causes some physiological changes (e.g., increase of intracellular $Ca^{2+}$, and the like) by binding, via C5a receptor, of "substances that bind to a C5a receptor" to a cell that expressed the C5a receptor.

The alkyl for $R^1$–$R^6$ and A includes, for example, linear or branched chain alkyl having 1 to 18 carbon atoms such as methyl, ethyl, propyl, isopropyl, butyl, isobutyl, secondary butyl, tertiary butyl, pentyl, 3-methylbutyl, neopentyl, 1-ethylpentyl, hexyl, 2-ethylbutyl, heptyl, octyl, decyl, hexadecyl, octadecyl and the like, and the like.

The alkoxy for $R^1$–$R^6$ includes, for example, linear or branched chain alkoxy having 1 to 18 carbon atoms such as methoxy, ethoxy, propoxy, isopropoxy, butoxy, isobutoxy, secondary butoxy, tertiary butoxy, pentyloxy, 3-methylbutoxy, neopentyloxy, hexyloxy, heptyloxy, octyloxy, decyloxy, hexadecyloxy, octadecyloxy and the like, and the like.

The halogen for $R^1$–$R^6$ is fluorine, chlorine, bromine or iodine.

The cycloalkyl for $R^1$–$R^3$ and A is exemplified by cycloalkyl having 3 to 7 carbon atoms, such as cyclopropyl, cyclopentyl, cyclohexyl and the like, and the like.

The aryl for $R^1$–$R^3$ and A is exemplified by aryl having 6 to 14 carbon atoms such as phenyl, 1-naphthyl, 2-naphthyl, 1-anthryl, 2-anthryl and the like. The aryl may be substituted by one or more substituents, wherein the position of the substitution is not particularly limited. The substituent may form a ring, and the ring may be condensed with aryl. When the substituent constitutes the ring, the ring may contain one or more hetero atoms such as nitrogen atom, oxygen atom, sulfur atom and the like. Examples thereof include benzo[d]1,3-dioxolen-5-yl, 2,3-dihydrobenzofuranyl and the like.

The heteroaryl for $R^1$–$R^3$ and A contains 5–14 atoms constituting the ring, and one or more hetero atoms such as nitrogen atom, oxygen atom, sulfur atom and the like. The heteroaryl may be substituted by one or more substituents and the position of substitution is not particularly limited. It may be monocyclic or polycyclic. The heteroaryl is preferably pyrrolyl, imidazolyl, pyrazolyl, isothiazolyl, thiazolyl, isoxazolyl, oxazolyl, thienyl, furyl, pyridyl, pyrazinyl, pyrimidinyl, pyridazinyl, indolyl, isoindolyl, indazolyl, benzofuranyl, benzothienyl, benzoxazolyl, benzimidazolyl, benzothiazolyl, quinolyl, isoquinolyl, quinoxalinyl, quinazolinyl, phenazinyl, tetrazolyl, oxadiazolyl and the like.

The alkenyl for $R^1$–$R^3$ is exemplified by linear or branched chain alkenyl having 2 to 8 carbon atoms such as vinyl, allyl, 1-propenyl, isopropenyl, 2-butenyl, 3-butenyl, 2-pentenyl, 4-pentenyl, 3-methyl-2-butenyl, 5-hexenyl, 4-methyl-3-pentenyl and the like, and the like.

The alkynyl for $R^1$–$R^3$ is exemplified by alkynyl having 2 to 5 carbon atoms such as ethynyl, propargyl, 2-butynyl, 5-pentynyl and the like, and the like.

The alkylthio for $R^1$–$R^3$ is exemplified by linear or branched chain alkylthio having 1 to 18 carbon atoms such as methylthio, ethylthio, propylthio, isopropylthio, butylthio, isobutylthio, secondary butylthio, tertiary butylthio, pentylthio, 3-methylbutylthio, neopentylthio, 1-ethylpentylthio, hexylthio, 2-ethylbutylthio, heptylthio, octylthio, decylthio, hexadecylthio, octadecylthio and the like, and the like.

The alkylamino for $R^1$–$R^3$ is lower alkylamino mono- or di-substituted by linear or branched chain lower alkyl having 1 to 3 carbon atoms, which is exemplified by methylamino, dimethylamino, ethylamino, diethylamino, propylamino, dipropylamino and the like.

The cyclic amino for $R^1$–$R^3$ has 3–8 atoms constituting the ring and may contain one or more oxygen atom, sulfur atom and nitrogen atom in the ring. Examples of cyclic amino include aziridyl, pyrrolidinyl, piperazino, piperidino, piperidyl, morpholino, morpholinyl, thiomorpholinyl, imidazolidinyl, heptamethyleneimino and the like.

The alkylsulfonyl for $R^1$–$R^3$ is linear or branched chain lower alkylsulfonyl having 1 to 3 carbon atoms, which is exemplified by methylsulfonyl, ethylsulfonyl, propylsulfonyl and the like.

The acyl for $R^1$–$R^3$ is exemplified by alkanoyl having 2 to 8 carbon atoms such as acetyl, propionyl, butyryl, isobutyryl, valeryl, isovaleryl, hexanoyl, octanoyl and the like, cycloalkylcarbonyl (cycloalkyl moiety is as defined for the aforementioned cycloalkyl) such as cyclopropylcarbonyl, cyclopentylcarbonyl, cyclohexylcarbonyl and the like, arylcarbonyl (aryl moiety is as defined for the aforementioned aryl) such as benzoyl, toluoyl, naphthoyl and the like, heteroarylcarbonyl (heteroaryl moiety is as defined for the aforementioned heteroaryl) such as nicotinoyl, thenoyl, furoyl and the like, and the like.

In acylamino for $R^1$–$R^3$, "acyl" is as defined above for acyl. In addition, alkylsulfonylamino and arylsulfonylamino are included in acylamino. The "alkyl" and "aryl" are as defined above. The acylamino is exemplified by acetamide, benzamide and the like.

The alkoxycarbonyl for $R^1$–$R^3$ is exemplified by alkoxycarbonyl wherein the alkoxy moiety is linear or branched chain alkoxy having 1 to 4 carbon atoms, such as methoxycarbonyl, ethoxycarbonyl, propoxycarbonyl, isopropoxycarbonyl, butoxycarbonyl, isobutoxycarbonyl, tertiary butoxycarbonyl and the like, and the like.

The alkylene for D is exemplified by alkylene having 1 to 10 carbon atoms such as methylene, ethylene, trimethylene, tetramethylene, pentamethylene, hexamethylene, octamethylene, nonamethylene, decamethylene and the like, and the like.

In the present invention, haloalkyl is linear or branched chain haloalkyl having 1 to 4 carbon atoms, which is exemplified by fluoromethyl, chloromethyl, bromomethyl, trifluoromethyl and the like.

In the present invention, haloalkyloxy is linear or branched chain haloalkyloxy having 1 to 4 carbon atoms, which is exemplified by 2,2,2-trifluoroethoxy, 2,2,3,3,3-pentafluoropropoxy and the like.

In the present invention, "aryl" of arylalkyl is as defined above for aryl, and "alkyl" is linear or branched chain lower alkyl having 1 to 3 carbon atoms. Examples of arylalkyl include benzyl, 2-phenylethyl, 3-phenylpropyl, 1-naphthylmethyl, 2-(1-naphthyl)ethyl, 2-naphthylmethyl, 2-(2-naphthyl)ethyl, 4-trifluoromethylbenzyl and the like.

In the present invention, "heteroaryl" of heteroarylalkyl is as defined above for heteroaryl and "alkyl" is linear or branched chain lower alkyl having 1 to 3 carbon atoms. Examples of heteroarylalkyl include 2-pyridylmethyl, 3-pyridylmethyl, 4-pyridylmethyl, 2-thienylmethyl, 3-thienylmethyl, 2-furylmethyl, 3-furylmethyl, 2-pyrrolylmethyl, 3-pyrrolylmethyl, 3-pyrazolylmethyl, 4-pyrazolylmethyl, 5-pyrazolylmethyl, 2-imidazolylmethyl, 4-imidazolylmethyl, 5-imidazolylmethyl, 2-oxazolylmethyl, 4-oxazolylmethyl, 5-oxazolylmethyl, 2-thiazolylmethyl, 4-thiazolylmethyl, 5-thiazolylmethyl, 2-(2-pyridyl)ethyl, 2-(3-pyridyl)ethyl, 2-(4-pyridyl)ethyl, 2-(2-thienyl)ethyl, 2-(3-thienyl)ethyl, 2-(2-thiazolyl)ethyl, 2-(4-thiazolyl)ethyl, 2-(5-thiazolyl)ethyl, (4-methyl-2-pyridyl)methyl and the like.

In the present invention, "aryl" of aryloxy is as defined above for aryl. The aryloxy is exemplified by phenoxy and the like.

In the present invention, "aryl" of arylalkyloxy is as defined above for aryl, and "alkyl" is linear or branched chain lower alkyl having 1 to 3 carbon atoms. The arylalkyloxy is exemplified by benzyloxy and the like.

In the present invention, alkylcarbamoyl is lower alkylcarbamoyl mono- or di-substituted with lower alkyl having 1 to 3 carbon atoms, which is exemplified by methylcarbamoyl, ethylcarbamoyl, dimethylcarbamoyl and the like.

The substituent of "optionally having a substituent" is exemplified by alkyl, cycloalkyl, haloalkyl, haloalkyloxy, alkenyl, alkynyl, hydroxy, alkoxy, mercapto, alkylthio, halogen, nitro, nitrile, amino, alkylamino, cyclic amino, alkylsulfonyl, carbamoyl, alkylcarbamoyl, acylamino, sulfamoyl, acyl, carboxy, alkoxycarbonyl, aryl, heteroaryl, arylalkyl, heteroarylalkyl, aryloxy, arylalkyloxy and the like, as defined above.

The pharmaceutically acceptable salt of the compound of the formula (1) is preferably exemplified by a salt with inorganic acid such as hydrochloric acid, hydrobromic acid, sulfuric acid, phosphoric acid, nitric acid and the like, a salt with organic acid such as acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, camphorsulfonic acid, ascorbic acid and the like, or a salt with metal such as alkali metal (lithium, sodium, potassium and the like), alkaline earth metal (calcium, magnesium and the like), aluminum and the like, salt with organic base such as piperidine, piperazine, morpholine, diethanolamine, ethylenediamine and the like.

The present invention encompasses solvates (e.g., hydrate) of the compound of the formula (1) or a salt thereof, prodrug metabolized in vivo to be converted to the compound of the formula (1), and active metabolites of the compound of the formula (1).

The compound of the present invention further encompasses any form of an optically pure enantiomer, a diastereomer and a mixture of these.

While the compound of the present invention can be produced by the following method, the production method is not limited to these.

The compound of the formula (1) can be synthesized by the route of the following methods 1–3.

Method 1

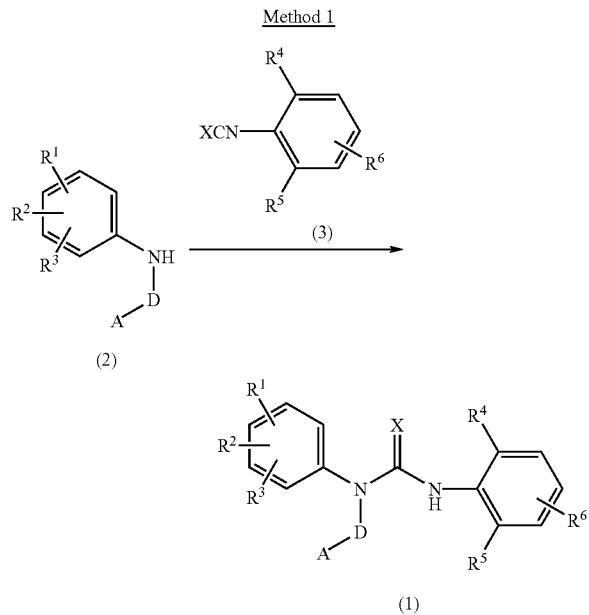

wherein $R^1$, $R^2$, $R^3$, $R^4$, $R^5$, $R^6$, A, D and X are as defined above.

That is, the compound of the formula (1) can be produced by reacting an aniline compound of the formula (2) with a compound of the formula (3) without solvent or in a suitable solvent.

The solvent to be used for the reaction is exemplified by methylene chloride, chloroform, benzene, toluene, xylene and the like. While the reaction temperature varies depending on the solvent, it is generally from 0° C. to 140° C., and while the reaction time varies depending on the reaction temperature, it is generally 1 hr to 72 hr.

Method 2

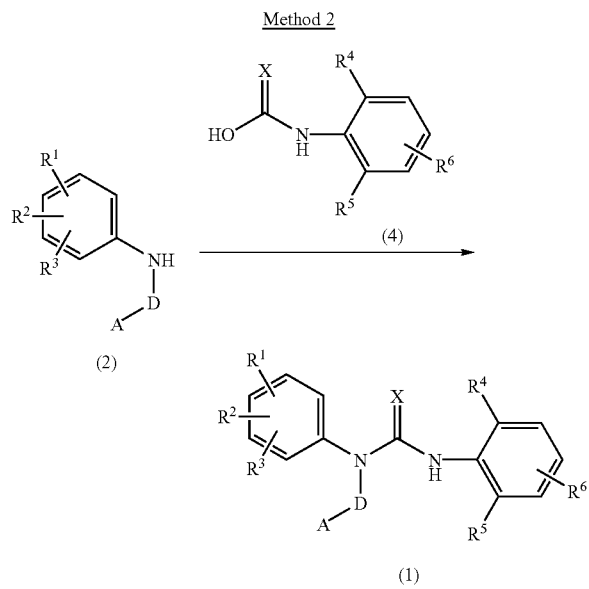

wherein $R^1$, $R^2$, $R^3$, $R^4$, $R^5$, $R^6$, A, D and X are as defined above.

That is, the compound of the formula (1) can be produced by reacting an aniline compound of the formula (2) or a salt thereof with a compound of the formula (4) or a reactive derivative thereof without solvent or in a suitable solvent.

The reaction between compound (2) or a salt thereof and compound (4) is carried out in the presence of a condensing agent such as carbodiimide(N,N'-dicyclohexylcarbodiimide, 1-ethyl-3-(3-dimethylaminopropyl)-carbodiimide and the like), diphenylphosphorylazide, N,N'-carbonyldiimidazole, 1-benzotriazolyloxy tris(dimethylamino)phosphonium hexafluorophosphate (Bop reagent), 2-chloro-N-methylpyridinium iodide-tributylamine system (Mukaiyama Method) and the like without solvent or in a suitable solvent preferably at −20° C. to 80° C. Generally, the reaction completes in 24 hr.

When the reactive derivative of compound (4) is acid halide (acid chloride and the like) or acid anhydride (symmetric acid anhydride, anhydrous lower alkylcarbonate mixture, anhydrous alkylphosphonate mixture and the like), the reaction is generally carried out without solvent or in a suitable solvent preferably in the presence of an acid scavenger of an organic base such as triethylamine, N-methylmorpholine, pyridine, dimethylaniline and the like or inorganic base such as sodium hydrogencarbonate, potassium carbonate, potassium hydroxide and the like at −20° C. to 80° C.

Moreover, when what is called an active ester (4-nitrophenyl ester, 4-chlorobenzyl ester, 4-chlorophenyl ester, succinimide ester, benzotriazole ester, 4-dimethylsulfonium phenyl ester and the like) is used as a reactive derivative, the reaction is generally carried out without solvent or in a suitable solvent at −20° C. to the refluxing temperature of the solvent.

The solvent to be used for the aforementioned reactions is exemplified by hydrocarbons such as hexane, benzene, toluene, xylene and the like, halogenated hydrocarbons such as chloroform, dichloromethane, dichloroethane and the like, ethers such as tetrahydrofuran, dioxane and the like, esters such as ethyl acetate and the like, ketones such as acetone, methyl ethyl ketone and the like, alcohols such as methanol, ethanol, isopropyl alcohol and the like, amides such as dimethylformamide, dimethylacetamide and the like, acetonitrile, dimethyl sulfoxide, water and a mixed solvent thereof and the like, and can be selected as appropriate depending on the reaction.

Method 3

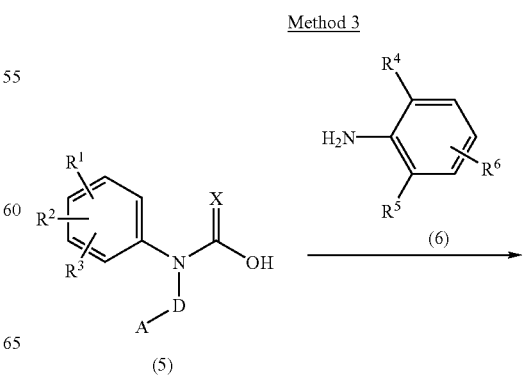

-continued

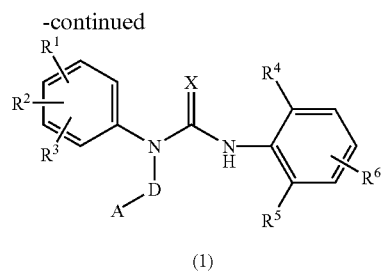

(1)

wherein $R^1$, $R^2$, $R^3$, $R^4$, $R^5$, $R^6$, A, D and X are as defined above.

That is, the compound of the formula (1) can be produced by reacting a compound of the formula (5) or a reactive derivative thereof with an aniline compound of the formula (6) or a salt thereof without solvent or in a suitable solvent.

The reaction between compound (5) and compound (6) or a salt thereof is carried out in the presence of a condensing agent such as carbodiimide (N,N'-dicyclohexylcarbodiimide, 1-ethyl-3-(3-dimethylaminopropyl)-carbodiimide and the like), diphenylphosphorylazide, N,N'-carbonyldiimidazole, 1-benzotriazolyloxy tris(dimethylamino)phosphonium hexafluorophosphate (Bop reagent), 2-chloro-N-methylpyridinium iodide-tributylamine system (Mukaiyama Method) and the like without solvent or in a suitable solvent preferably at −20° C. to 80° C. Generally, the reaction completes in 24 hr.

When the reactive derivative of compound (5) is an acid halide (acid chloride and the like) or an acid anhydride (symmetric acid anhydride, anhydrous lower alkylcarbonate mixture, anhydrous alkylphosphonate mixture and the like), the reaction is generally carried out without solvent or in a suitable solvent preferably in the presence of an acid scavenger of organic base such as triethylamine, N-methylmorpholine, pyridine, dimethylaniline and the like or inorganic base such as sodium hydrogencarbonate, potassium carbonate, potassium hydroxide and the like at −20° C. to 80° C.

Furthermore, when what is called an active ester (4-nitrophenyl ester, 4-chlorobenzyl ester, 4-chlorophenyl ester, succinimide ester, benzotriazole ester, 4-dimethylsulfonium phenyl ester and the like) is used as a reactive derivative, the reaction is generally carried out without solvent or in a suitable solvent at −20° C. to the refluxing temperature of the solvent.

The inert solvent to be used in the aforementioned reactions is exemplified by hydrocarbons such as hexane, benzene, toluene, xylene and the like, halogenated hydrocarbons such as chloroform, dichloromethane, dichloroethane and the like, ethers such as tetrahydrofuran, dioxane and the like, esters such as ethyl acetate and the like, ketones such as acetone, methyl ethyl ketone and the like, alcohols such as methanol, ethanol, isopropyl alcohol and the like, amides such as dimethylformamide, dimethylacetamide and the like, acetonitrile, dimethyl sulfoxide, water and a mixed solvent thereof and the like, and can be selected as appropriate depending on the reaction.

Method 4

Of the compounds of the formula (1), a compound wherein A is alkoxyphenyl can be synthesized by the following route.

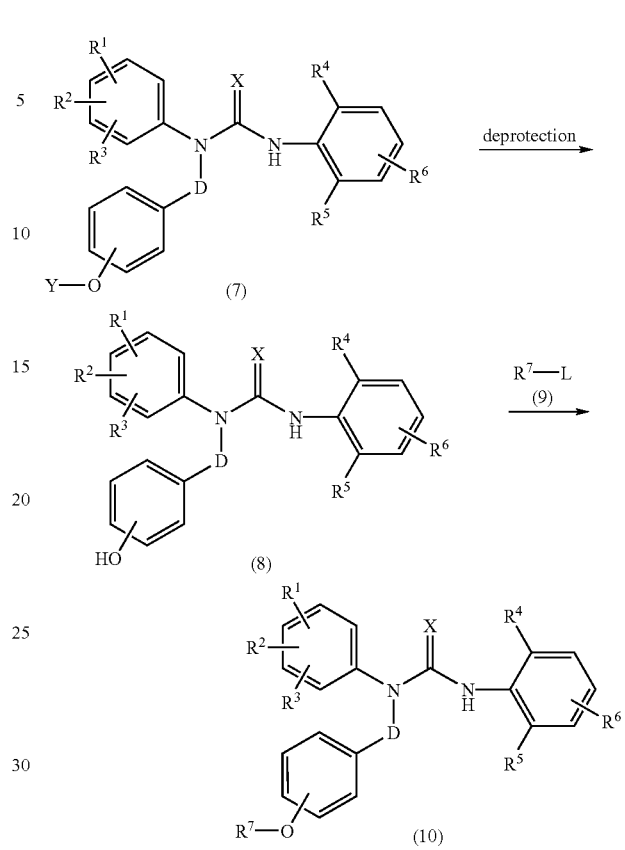

wherein $R^1$, $R^2$, $R^3$, $R^4$, $R^5$, $R^6$, D and X are as defined above, $R^7$ is alkyl optionally having a substituent, and the like, protecting group Y is methyl, benzyl, substituted benzyl, benzyloxycarbonyl and the like, and L is chlorine, bromine, iodine, methanesulfonyloxy, p-toluenesulfonyloxy, trifluoromethanesulfonyloxy and the like.

That is, a protecting group Y of a urea compound of the formula (7) is removed in a suitable solvent to give a phenol compound of the formula (8), which is then reacted with a compound of the formula (9) in the presence of a base in a suitable solvent, whereby a compound of the formula (10) can be produced.

The protecting group can be removed by a typical method such as hydrolysis, acid treatment, reduction and the like according to a conventional method depending on the kind of the protecting group.

The reaction between compound (8) and compound (9) is carried out without solvent or in a suitable solvent that does not inhibit the reaction, preferably in the presence of a acid scavenger of an organic base such as triethylamine, N-methylmorpholine, pyridine, dimethylaniline and the like or an inorganic base such as alkali hydrogencarbonate, alkali carbonate, alkali hydroxide and the like at −20° C. to the refluxing temperature of the solvent.

The solvent to be used is exemplified by hydrocarbons such as hexane, benzene, toluene, xylene and the like, halogenated hydrocarbons such as chloroform, dichloromethane, dichloroethane and the like, ethers such as tetrahydrofuran, dioxane and the like, esters such as ethyl acetate and the like, ketones such as acetone, methyl ethyl ketone and the like, alcohols such as methanol, ethanol, isopropyl alcohol and the like, amides such as dimethylformamide, dimethylacetamide and the like, acetonitrile, dimethyl sulfoxide, water and a mixed solvent thereof and the like, and can be selected as appropriate depending on the reaction.

The aniline, which is a starting material, can be synthesized by the following methods 5–7.

Method 5

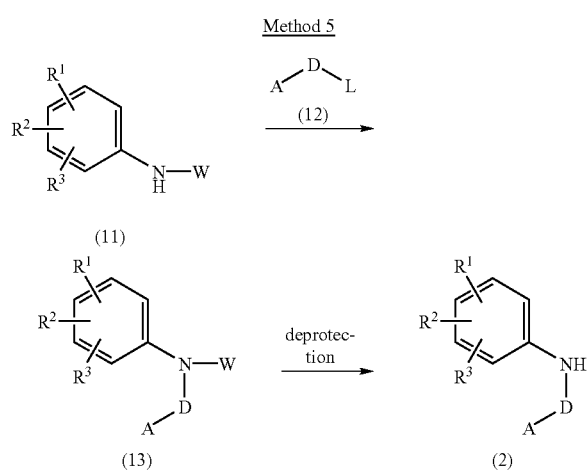

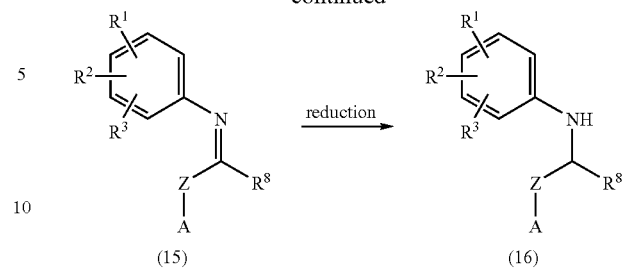

wherein $R^1$, $R^2$, $R^3$ and A are as defined above, Z is alkylene optionally having a substituent, and $R^8$ is hydrogen, alkyl optionally having a substituent, aryl optionally having a substituent, heteroaryl optionally having a substituent and the like.

wherein $R^1$, $R^2$, $R^3$, A, D and L are as defined above, and W is acetyl, tert-butoxycarbonyl and the like.

That is, a compound of the formula (11) and a compound of the formula (12) are reacted in the presence of a base in a suitable solvent to give a compound of the formula (13), and then the compound is deprotected, whereby the aniline compound of the formula (2) can be produced.

The solvent to be used for this reaction is exemplified by methanol, ethanol, propanol, isopropyl alcohol, methylene chloride, chloroform, tetrahydrofuran, dioxane, benzene, toluene, xylene, dimethylformamide, dimethyl sulfoxide and the like. The base to be used is exemplified by sodium hydride, sodium carbonate, potassium carbonate, sodium hydrogencarbonate, sodium hydroxide, potassium hydroxide, triethylamine, diisopropylethylamine, pyridine and the like. While the reaction temperature varies depending on the solvent, it is generally from 0° C. to 140° C. and while the reaction time varies depending on the reaction temperature, it is generally from 1 hr to 24 hr.

This reaction can be carried out without protecting group W, whereby compound (2) can be obtained.

The protecting group can be removed by a typical method such as hydrolysis, acid treatment and the like according to a conventional method depending on the kind of the protecting group.

That is, a compound of the formula (11) and aldehyde or ketone of the formula (14) are subjected to dehydration condensation without solvent or in a suitable solvent to give a compound of the formula (15), which is then subjected to catalytic reduction or reacted with a reducing agent in a suitable solvent, whereby a compound of the formula (16) can be produced.

The dehydration condensation reaction between compound (11) and compound (14) can be carried out in the presence of a dehydrating agent or by removing generated water using a Dean-Stark trap from the reaction system.

As a dehydrating agent to be used for this reaction, a general dehydrating agent can be used. The dehydrating agent is exemplified by magnesium sulfate, molecular sieves and the like. The solvent to be used for the reaction is exemplified by methylene chloride, chloroform, benzene, toluene, xylene and the like. While the reaction temperature varies depending on the solvent, it is generally from room temperature to the refluxing temperature of the solvent and while the reaction time varies depending on the reaction temperature, it is generally from 1 hr to 24 hr.

As the reducing agent to be used for the reduction, sodium borohydride, sodium cyanoborohydride, formic acid, sodium formate and the like can be mentioned. The solvent to be used for the reduction is exemplified by water, methanol, ethanol, propanol, tetrahydrofuran, dioxane, acetic acid and the like, and it may be a mixed solvent thereof. While the reaction temperature varies depending on the solvent, it is generally from 0° C. to 80° C. and while the reaction time varies depending on the reaction temperature, it is generally from 1 hr to 24 hr.

Method 6

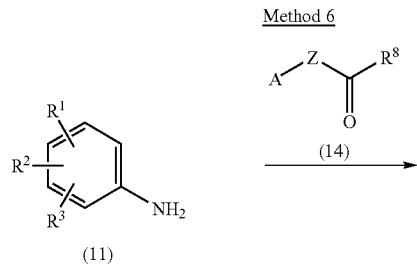

Method 7

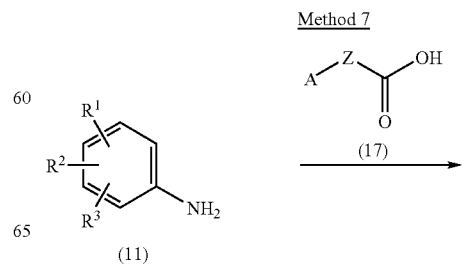

-continued

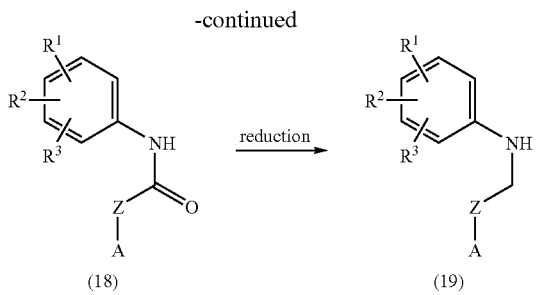

wherein R¹, R², R³, A and Z are as defined above.

That is, a compound of the formula (11) or a salt thereof is reacted with carboxylic acid of the formula (17) or a reactive derivative thereof without solvent or in a suitable solvent to give an amide compound of the formula (18), which is then reacted with a reducing agent in a suitable solvent, whereby a compound of the formula (19) can be produced.

For example, the reaction between compound (11) or a salt thereof and compound (17) is carried out in the presence of a condensing agent such as carbodiimide (N,N'-dicyclohexylcarbodiimide, 1-ethyl-3-(3-dimethylaminopropyl)-carbodiimide and the like), diphenylphosphorylazide, N,N'-carbonyldiimidazole, 1-benzotriazolyloxy tris(dimethylamino)phosphonium hexafluorophosphate (Bop reagent), 2-chloro-N-methylpyridinium iodide-tributylamine system (Mukaiyama Method) and the like in an inert solvent or without solvent preferably at −20° C. to 80° C. Generally, the reaction completes in 24 hr.

When the reactive derivative of compound (17) is an acid halide (acid chloride, acid bromide and the like) or an acid anhydride (symmetric acid anhydride, anhydrous lower alkylcarbonate mixture, anhydrous alkylphosphate mixture and the like), the reaction is generally carried out without solvent or in a suitable solvent preferably in the presence of a acid scavenger of an organic base such as triethylamine, N-methylmorpholine, pyridine, dimethylaniline and the like or an inorganic base such as alkali hydrogencarbonate, alkali carbonate, alkali hydroxide and the like at −20° C. to 80° C.

Furthermore, when what is called an active ester (4-nitrophenyl ester, 4-chlorobenzyl ester, 4-chlorophenyl ester, succinimide ester, benzotriazole ester, 4-dimethylsulfonium phenyl ester and the like) is used as a reactive derivative, the reaction is generally carried out without solvent or in a suitable solvent at −20° C. to the refluxing temperature of the solvent.

The solvent to be used for the aforementioned amidation reaction may be, for example, hydrocarbons such as hexane, benzene, toluene and the like, halogenated hydrocarbons such as chloroform, dichloromethane, dichloroethane and the like, ethers such as tetrahydrofuran, dioxane and the like, esters such as ethyl acetate and the like, ketones such as acetone, methyl ethyl ketone and the like, alcohols such as methanol, ethanol, isopropyl alcohol and the like, amides such as dimethylformamide, dimethylacetamide and the like, acetonitrile, dimethyl sulfoxide, water, a mixed solvent thereof and the like, and can be selected as appropriate depending on the reaction.

The reducing agent to be used for the reduction is exemplified by lithium aluminum hydride, borane and the like. The solvent to be used for the reduction is exemplified by tetrahydrofuran, diethyl ether, hexane and the like, or a mixed solvent thereof may be used. While the reaction temperature varies depending on the solvent, it is generally from 0° C. to the refluxing temperature of the solvent and while the reaction time varies depending on the reaction temperature, it is generally from 1 hr to 24 hr.

A part of the compound of the formula (1) according to the present invention can be converted to a desired salt by a treatment with an acid or a base as necessary in a suitable solvent (methanol, ethanol and the like). Examples thereof include inorganic acid addition salt (e.g., salt with hydrochloric acid, hydrobromic acid, hydroiodic acid, sulfuric acid, nitric acid, phosphoric acid and the like), organic acid addition salt (e.g., salt with methanesulfonic acid, ethanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, benzoic acid, lactic acid, salicylic acid, gallic acid, picric acid, carbonic acid, ascorbic acid, malic acid and the like) and the like. In addition, a salt may be obtained using oxalic acid for crystallization.

In the same manner as above, the compound of the formula (1) can be converted to, for example, alkali metal salt (e.g., salt with lithium, sodium, potassium and the like), alkaline earth metal (e.g., salt with calcium, magnesium and the like), aluminum salt, ammonium salt, salt with organic base salt (e.g., salt with triethylamine, morpholine, piperidine, triethanolamine, tris-hydroxymethylaminomethane and the like), or salt with amino acid (e.g., salt with alanine, phenylalanine, histidine, lysin, arginine, glutamic acid, aspartic acid and the like).

Moreover, the compound of the formula (1) or a pharmaceutically acceptable salt thereof can show polymorphism and can be present as more than one tautomer, and also can be present as a solvate (e.g., ketone solvate, hydrate and the like). Accordingly, the present invention encompasses any of the above-mentioned polymorphic form or solvate thereof, any mixture thereof and the like.

The compound of the present invention, a pharmaceutically acceptable salt thereof and a solvate thereof show a C5a receptor antagonistic action and are useful as a prophylactic or therapeutic drug of diseases or syndromes due to inflammation caused by C5a [e.g., autoimmune diseases such as rheumatism and systemic lupus erythematosus and the like, sepsis, adult respiratory distress syndrome, chronic obstructive pulmonary disease, allergic diseases such as asthma and the like, atherosclerosis, cardiac infarction, brain infarction, psoriasis, Alzheimer's disease and serious organ injury (e.g., pneumonia, nephritis, hepatitis and pancreatitis and the like) due to activation of leukocytes caused by ischemia, trauma, burn, surgical invasion and the like. In addition, they are useful as a prophylactic or therapeutic drug of infectious diseases due to bacteria or virus that invades via a C5a receptor.

When the compound of the present invention of the formula (1) is used for the aforementioned prophylaxis or treatment, it is generally administered systemically or topically and orally or parenterally. The dose to patients varies depending on the age, body weight, sex, general health conditions, treatment effect, diet, administration time, administration method, clearance rate, combination of drugs, the condition of the disease under treatment and the like. It is generally desirably in the range of from 0.1 mg to 500 mg per dose for an adult by oral administration once to several times a day, or in the range of from 0.01 mg to 200 mg per dose for an adult by parenteral administration (preferably intravenous administration) once to several times a day.

As mentioned above, because the dose may change depending on various conditions, a dose smaller than the above-mentioned range may be sufficient or a dose exceeding the above-mentioned range may be necessary.

The compound of the present invention, a pharmaceutically acceptable salt thereof and a solvate thereof can be used orally or parenterally by inhalation, rectal administration or topical administration as a pharmaceutical composition or preparation (e.g., powder, granule, tablet, pill, capsule, syrup, elixir, suspension, solution and the like), wherein at least one compound of the present invention can be used alone or used upon admixing with a pharmaceutically acceptable carrier (excipient, binder, disintegrant, corrigent, corrective, emulsifier, diluent and/or dissolution aids and the like).

A pharmaceutical composition can be prepared according to a general method. In the present specification, by the parenteral is meant subcutaneous injection, intravenous injection, intramuscular injection, intraperitoneal injection, drip and the like. A composition for injection, such as sterile suspension for injection and oil suspension can be prepared using a suitable dispersing agent, wetting agent, or suspending agent according to a method known in the art.

A solid composition for oral administration is exemplified by tablet, pill, capsule, powder, granule and the like. In the above-mentioned solid composition, one or more active compounds can be admixed with at least one additive such as sucrose, lactose, mannitol, multitol, glucose, hydroxypropylcellulose, microcrystalline cellulose, starch, polyvinylpyrrolidone, magnesium aluminometasilicate, dextran, starches, agar, arginates, chitins, chitosans, pectins, tragacanth gums, Acacia, gelatins, collagens, casein, albumin, synthetic or semi-synthetic polymers or gliccrides.

In addition, the above-mentioned composition can contain further additives such as lubricants (e.g., magnesium stearate etc.), preservatives (e.g., parabens, sorbins etc.), antioxidants (e.g., ascorbic acid, α-tocopherol, cysteine etc.), disintegrants (e.g., carmellose calcium etc.), stabilizers (e.g., lactose etc.), dissolution aids (e.g., glutamic acid, aspartic acid etc.), binder, thickener, sweetener, flavor, perfume and the like.

Where necessary, the tablet and pill may be coated with a film of gastric or enteric coating such as sucrose, gelatin, hydroxypropylcellulose, hydroxypropylmethylcellulose phthalate and the like, or may be coated with two or more layers. In addition, they may include a capsule of absorbable material such as gelatin.

The liquid composition for oral administration includes pharmaceutically acceptable solution, suspension, syrup, elixir and the like, and may contain a generally used inactive diluent (purified water, ethanol). This composition may contain, besides the inactive diluent, auxiliaries such as wetting agent, suspending agent, sweetening agent, flavor, perfume and preservative.

Other compositions for oral administration are, for example, spray agent containing one or more active substances and formulated by a method known per se.

The composition for injection for parenteral administration may include sterile aqueous or non-aqueous solution, suspension and emulsion. Examples of the aqueous solution and suspension include distilled water for injection and physiological saline. Examples of the water insoluble solution and suspension include propylene glycol, polyethylene glycol, olive oil, ethanol, polysorbate 80 and the like. The above-mentioned composition may further contain auxiliaries such as preservative, wetting agent, emulsifier, dispersing, agent, stabilizer (e.g., lactose and the like) and dissolution aids (e.g., amino acid such as arginine, glutamic acid, aspartic acid, and the like). These can be sterilized by, for example, filtration through a bacteria-retaining filter, addition of microbicide or UV irradiation and the like.

The composition for injection can be used by producing a sterile solid composition and dissolved, for example, the lyophilized product in sterile water or sterile solvent for injection before use.

Other composition for parenteral administration include external solution, ointment, liniment, suppository and the like, containing one or more active substances and formulated by a conventional method.

The suppository for rectal administration can be produced by admixing the drug and a suitable non-irritant vehicle, which is a substance which is solid at ambient temperature but liquid at the temperature of intestine and which melts in the rectum to release the drug, such as cocoa butter and polyethylene glycols.

The compound of the formula (1) of the present invention or a pharmaceutically acceptable salt thereof is expected to show a superior treatment effect by a combined use with an agent for the prophylaxis or treatment of autoimmune diseases, sepsis, adult respiratory distress syndrome, chronic obstructive pulmonary disease, allergic diseases such as asthma and the like, atherosclerosis, cardiac infarction, brain infarction, psoriasis, Alzheimer's disease, ischemia, trauma, burn or serious organ injury. As used herein, by the "combined use" is meant a combination composition of the compound of the present invention or a pharmaceutically acceptable salt thereof with an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury, and the use as a potentiator of an action of an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury, including combined use and concurrent use, wherein two or more active ingredient compounds are simultaneously used with or without mixing or used in a staggered manner. The pharmaceutical drug of the present invention which is characterized by the combined use of the compound represented by the above-mentioned formula (1) or a pharmaceutically acceptable salt thereof and an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury, is not particularly limited in terms of the mode of use thereof as long as the compound represented by the formula (1) or a pharmaceutically acceptable salt thereof and an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury are combined. For example, (A) the compound represented by the formula (1) or a pharmaceutically acceptable salt thereof, and (B) an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury may be formulated as preparations to be each generally administered, or a composition wherein they are combined in advance may be used. The combined pharmaceutical drug of the present invention may be, for example, a single agent obtained by mixing the compound represented by the formula (1) or a pharmaceutically acceptable salt thereof and an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury according to a known production method for pharmaceutical preparations using, where desired, pharmaceutically acceptable diluent, excipient and the like, or respective preparations thereof obtained using, where desired, pharmaceutically acceptable diluent, excipient and the like, or a combination preparation in a container including respective preparations thereof (set, kit, pack). For example, the combined pharmaceutical drug of the present invention can be used as a combination preparation packaging the same or different preparations of a preparation containing the compound represented by the formula (1) or a pharmaceutically acceptable salt thereof, and an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury, or as a composition containing the compound represented by the formula (1) or a pharmaceutically acceptable salt thereof and an agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury.

When the compound of the present invention or a pharmaceutically acceptable salt thereof is used as a combination composition, the ratio of the composition is optional, and the amount of the compound of the present invention or a pharmaceutically acceptable salt thereof to be mixed can be determined depending on the kind of the various pharmaceutical agents to be mixed for combination, and the factors such as titer and the like. When it is used as a combination drug, the dose of the compound of the present invention or a pharmaceutically acceptable salt thereof, and the pharmaceutical agent to be combined therewith can be determined as appropriate from the range generally employed. It is preferable to administer in a smaller dose than the dose for single use of each pharmaceutical agent, in the hope of affording a synergistic effect.

Examples of the agent for the prophylaxis or treatment of autoimmune disease, sepsis, adult respiratory distress syndrome, chronic obstructive pulmonary disease, allergic disease such as asthma and the like, atherosclerosis, cardiac infarction, brain infarction, psoriasis, Alzheimer's disease, ischemia, trauma, burn or serious organ injury include antirheumatic agents (gold compound, penicillamine, bucillamine, lobenzarit, actarit, salazosulfapyridine etc.), immunosuppressants (azathioprine, cyclophosphamide, methotrexate, brequinar sodium, deoxyspergualin, mizoribine, 2-morpholinoethyl mycophenolate, cyclosporin, rapamycin, tacrolimus hydrate, leflunomide, OKT-3, anti-TNF-α antibody, anti-IL (interleukin)-6 antibody and FTY720 (EP627406-B1) etc.), steroidal drugs (predonizolone, methylpredonizolone, dexamethazone, hydrocortizone etc.) or nonsteroidal anti-inflammatory agents (aspirin, indometacin, indometacin farnesylate, diclofenac sodium, alclofenac, amfenac sodium, ibuprofen, ketoprofen, loxoprofen sodium, naproxen, pranoprofen, zaltoprofen, mefenamic acid, flufenamic acid, tolfenamic acid, phenylbutazone, ketophenylbutazone, piroxicam, tenoxicam, ampiroxicam etc.), bactericides (gentamicin, tobramycin, cefotaxim, ceftazidime, vancomycin, erythromycin, imipenem, metronidazole etc.), cerebral circulatory metabolism improvers (meclofenoxate, idebenone, indeloxazine, nicergoline, propentofylline, cytochrome C, citicoline, ifenprodil, bencyclane, cinepazide, ozagrel, nizofenone, ibudilast, pentoxifylline, propentofylline, vinpocetine, brovincamine, dihydroergotoxine, moxisylyte, dilazep, nicardipine, cinnarizine, flunarizine, nilvadipine etc.), anti-platelet aggregation inhibitors (ticlopidine, aspirin, beraprost, dipyridamole, cilostazol, ozagrel, sarpogrelate etc.), anticoagulants (heparin, warfarin etc.), thrombolytic agents (urokinase, tissue plasminogen activator etc.), antiallergic agents (cromoglic acid, pranlukast, ozagrel, seratrodast, tranilast, amlexanox, repirinast, tazanolast, pemirolast, ibudilast, supratast, ketotifen, azelastine, oxatomide, terfenadine, mequitazine, epinastine, astemizole, ramatroban, zafirlukast etc.), proteolytic enzyme inhibitors (gabexate, nafamosutat, aprotinin etc.), acetylcholinesterase inhibitors (aricept etc.) and the like.

EXAMPLES

The present invention is specifically explained in the following by referring to Preparation Examples, Examples, Formulation Examples and Test Examples, which are not to be construed as limitative.

Preparation Example 1

To a solution of benzaldehyde (10 mL) in toluene (200 mL) were added, under ice-cooling, 4-octylaniline (22.5 mL) and molecular sieves 4A (20 g), and the mixture was stirred overnight at room temperature. The molecular sieves 4A was filtered off from the reaction mixture and the obtained filtrate was concentrated under reduced pressure. The residue was dissolved in methanol (200 mL) and sodium borohydride (2.3 g) was added under ice-cooling. The mixture was stirred at room temperature for 5 hr. Methanol was evaporated and water was added to the residue. The mixture was extracted with chloroform and the organic layer was washed with saturated brine, dried and concentrated under reduced pressure to give benzyl(4-octylphenyl)amine (29 g).

$^1$H-NMR(CDCl$_3$)δ: 0.85(3H, t, J=6.6 Hz), 1.27–1.30(10H, m), 1.59(2H, t, J=7.3 Hz), 2.58(2H, t, J=7.3 Hz), 4.29(2H, s), 6.56(2H, d, J=8.6 Hz), 6.97(2H, d, J=8.6 Hz), 7.26–7.38(5H, m).

Preparation Example 2

By the reaction and treatment in the same manner as in Preparation Example 1 using 4-methoxybenzaldehyde (1.0 g) and 4-octylaniline (1.4 g) as starting materials, [(4-methoxyphenyl)methyl](4-octylphenyl)amine (2.2 g) was obtained.

$^1$H-NMR(CDCl$_3$)δ: 0.90(3H, t, J=6.6 Hz), 1.22–1.51(10H, m), 1.54(2H, t, J=7.9 Hz), 2.48(2H, t, J=7.9 Hz), 3.79(3H, s), 4.22(2H, s), 6.57(2H, d, J=8.6 Hz), 6.86 (2H, d, J=8.6 Hz), 6.98(2H, d, J=8.9 Hz), 7.28(2H, d, J=8.9 Hz).

Preparation Example 3

By the reaction and treatment in the same manner as in Preparation Example 1 using 4-hydroxybenzaldehyde and 4-octylaniline as starting materials, [(4-hydroxymethylphenyl)methyl](4-octylphenyl)amine was obtained.

Preparation Example 4

By the reaction and treatment in the same manner as in Preparation Example 1 using 4-dimethylaminobenzaldehyde (0.75 g) and 4-octylaniline (1.0 g) as starting materials, [(4-dimethylaminophenyl)methyl](4-octylphenyl)amine (1.1 g) was obtained.
$^1$H-NMR(CDCl$_3$)δ: 0.87(3H, t, J=6.8 Hz), 1.22–1.41(10H, m), 1.53(2H, t, J=7.9 Hz), 2.48(2H, t, J=7.9 Hz), 2.92(6H, s), 4.17(2H, s), 6.58(2H, d, J=8.0 Hz), 6.70(2H, d, J=8.0 Hz), 6.98(2H, d, J=8.0 Hz), 7.23(2H, d, J=8.0 Hz).

Preparation Example 5

By the reaction and treatment in the same manner as in Preparation Example 1 using 4-dimethylaminobenzaldehyde (10.0 g) and 4-butylaniline (10.0 g) as starting materials, (4-butylphenyl)[(4-dimethylaminophenyl)methyl]amine (6.83 g) was obtained. melting point: 60–61° C.

Preparation Example 6

By the reaction and treatment in the same manner as in Preparation Example 1 using 4-dimethylaminobenzaldehyde (10.0 g) and 4-methoxyaniline (8.25 g) as starting materials, [(4-dimethylaminophenyl)methyl](4-methoxyphenyl)amine (5 g) was obtained. melting point: 92–94° C.

Preparation Example 7

By the reaction and treatment in the same manner as in Preparation Example 1 using 4-dimethylaminobenzaldehyde (10 g) and 4-ethylaniline (8.12 g) as starting materials, [(4-dimethylaminophenyl)methyl](4-ethylphenyl)amine (10.7 g) was obtained. melting point: 64–66° C.

Preparation Example 8

By the reaction and treatment in the same manner as in Preparation Example 1 using 4-dimethylaminobenzaldehyde (11 g) and 4-propylaniline (10 g) as starting materials, [(4-dimethylaminophenyl)methyl](4-propylphenyl)amine (17.6 g) was obtained. melting point: 74–76° C.

Preparation Example 9

By the reaction and treatment in the same manner as in Preparation Example 1 using 4-dimethylaminobenzaldehyde (11 g) and 4-isopropylaniline (10 g) as starting materials, [(4-dimethylaminophenyl)methyl](4-isopropylphenyl)amine (13.6 g) was obtained. melting point: 71–73° C.

Preparation Example 10

By the reaction and treatment in the same manner as in Preparation Example 1 using 4-dimethylaminobenzaldehyde (11 g) and 4-ethoxyaniline (10 g) as starting materials, [(4-dimethylaminophenyl)methyl](4-ethoxyphenyl)amine (8.7 g) was obtained. melting point: 98–99° C.

Preparation Example 11

By the reaction and treatment in the same manner as in Preparation Example 1 using 4-isopropylbenzaldehyde (1.5 g) and 4-isopropylaniline (1.4 g) as starting materials, (4-isopropylphenyl)[(4-isopropylphenyl)methyl]amine (2.6 g) was obtained.
$^1$H-NMR(CDCl$_3$)δ: 1.20(6H, d, J=7.3 Hz), 1.24(6H, d, J=7.3 Hz), 2.80(1H, m), 2.90(1H, m), 3.84(1H, s),4.25(2H, s), 6.58(2H, d, J=8.6 Hz), 7.04(2H, d, J=8.6 Hz), 7.19(2H, d, J=7.9 Hz), 7.29(2H, d, J=7.9 Hz).

Preparation Example 12

By the reaction and treatment in the same manner as in Preparation Example 1 using 4-dimethylaminobenzaldehyde (1.5 g) and 3,4-dimethylaniline (1.2 g) as starting materials, [(4-dimethylaminophenyl)methyl](3,4-dimethylphenyl)amine (1.4 g) was obtained. melting point: 73–75° C.

Preparation Example 13

To a solution of N-(4-isopropylphenyl)acetamide (1.8 g) in dimethylformamide (18 mL) was added, under ice-cooling, 60% sodium hydride (0.44 g). Further, butyl bromide (1.4 mL) was added and the mixture was stirred overnight. Water was added to the reaction mixture, and the mixture was extracted with ethyl acetate. The organic layer was washed, dried and concentrated under reduced pressure. 4N Hydrochloric acid (13 mL) was added to the residue and the mixture was refluxed for 7 hr. Water was added to the reaction mixture followed by neutralization and the mixture was extracted with ethyl acetate. The organic layer was washed, dried and concentrated under reduced pressure to give butyl(4-isopropylphenyl)amine (1.8 g).

Preparation Example 14

By the reaction and treatment in the same manner as in Preparation Example 1 using 4-dimethylaminobenzaldehyde (1.8 g) and 3,4-dichloroaniline (1.4 g) as starting materials, (3,4-dichlorophenyl)[(4-isopropylphenyl)methyl]amine (2.6 g) was obtained.
$^1$H-NMR(CDCl$_3$)δ: 1.19(6H, d, J=6.6 Hz), 2.80(1H, m), 3.84(1H, s), 4.26(2H, s), 6.53(2H, d, J=8.6 Hz), 7.03(2H, d, J=8.6 Hz), 7.18(1H, dd, J=2.0, 8.0 Hz), 7.37(1H, d,J=8.0 Hz), 7.45(1H, d, J=2.0 Hz).

Preparation Example 15

By the reaction and treatment in the same manner as in Preparation Example 1 using 2,4-dimethoxybenzaldehyde (8.0 g) and 4-isopropylaniline (1.4 g) as starting materials, [(2,4-dimethoxyphenyl)methyl](4-isopropylphenyl)amine (11 g) was obtained.
$^1$H-NMR(CDCl$_3$)δ: 1.19(6H, d, J=7.3 Hz), 2.70–2.82(1H, m), 4.19(2H, s), 5.91(2H, s), 6.57(2H, d, J=8.6 Hz), 6.59–6.86(4H, m), 7.03(2H, d, J=8.6 Hz).

Preparation Example 16

By the reaction and treatment in the same manner as in Preparation Example 1 using 4-dimethylaminobenzaldehyde (1.5 g) and 2,4-dimethylaniline (1.2 g) as starting materials, [(4-dimethylaminophenyl)methyl](2,4-dimethylphenyl)amine (2.4 g) was obtained. melting point: 79–80° C.

Preparation Example 17

By the reaction and treatment in the same manner as in Preparation Example 1 using piperonal (4.5 g) and 4-isopropylaniline (4.0 g) as starting materials, (benzo[d]1,3-dioxolen-5-ylmethyl)(4-isopropylphenyl)amine (6.1 g) was obtained.
$^1$H-NMR(CDCl$_3$)δ: 1.19(6H, d, J=7.3 Hz), 2.70–2.82(1H, m), 3.78(3H, s), 3.81(3H, s), 4.21(2H, s), 6.40–6.46(2H, m), 6.60(2H, d, J=8.6 Hz), 7.03(2H, d, J=8.6 Hz), 7.03(1H, d, J=8.0 Hz).

Preparation Example 18

By the reaction and treatment in the same manner as in Preparation Example 1 using 2,4-dimethylbenzaldehyde (1.3 g) and 4-isopropylaniline (1.4 g) as starting material, [(2,4-dimethylphenyl)methyl](4-isopropylphenyl)amine (2.4 g) was obtained.
$^1$H-NMR(CDCl$_3$)δ: 1.20(6H, d, J=7.3 Hz), 2.30(3H, s), 2.32(3H, s), 2.83(1H, m), 3.84(1H, s), 4.19(2H, s), 6.57(2H, d, J=8.6 Hz), 7.03(2H, d, J=8.6 Hz), 6.89–7.22(5H,m).

Preparation Example 19

By the reaction and treatment in the same manner as in Preparation Example 1 using 4-fluorobenzaldehyde (1.2 g) and 4-isopropylaniline (1.4 g) as starting materials, [(4-fluorophenyl)methyl](4-isopropylphenyl)amine (2.2 g) was obtained.
$^1$H-NMR(CDCl$_3$)δ: 1.20(6H, d, J=6.6 Hz), 2.80(1H, m), 3.84(1H, s), 4.26(2H, s), 6.57(2H, d, J=8.8 Hz), 6.97–7.05 (4H, m), 7.30–7.35(2H, m).

Preparation Example 20

By the reaction and treatment in the same manner as in Preparation Example 1 using 4-trifluorbmethylbenzaldehyde (1.7 g) and 4-isopropylaniline (1.4 g) as starting materials, (4-isopropylphenyl)[(4-trifluoromethylphenyl)methyl]amine (2.4 g) was obtained.
$^1$H-NMR(CDCl$_3$)δ: 1.19(6H, d, J=6.6 Hz), 2.80(1H, m), 3.84(1H, s), 4.38(2H, s), 6.56(2H, d, J=8.6 Hz), 7.04(2H, d, J=8.6 Hz), 7.47(2H, d, J=8.8 Hz), 7.58(2H, d, J=8.8 Hz).

Preparation Example 21

By the reaction and treatment in the same manner as in Preparation Example 1 using 2,4-dichlorobenzaldehyde (1.8 g) and 4-isopropylaniline (1.4 g) as starting materials, [(2,4-dichlorophenyl)methyl](4-isopropylphenyl)amine (2.7 g) was obtained.
$^1$H-NMR(CDCl$_3$)δ: 1.17(6H, d, J=7.2 Hz), 2.79(1H, m), 4.36(2H, s), 6.53(2H, d, J=8.6 Hz), 7.03(2H, d, J=8.6 Hz), 7.14–7.19(1H, m), 7.33–7.38(2H, m).

Preparation Example 22

By the reaction and treatment in the same manner as in Preparation Example 1 using 4-methylthiobenzaldehyde (5.0 g) and 4-isopropylaniline (4.4 g) as starting materials, (4-isopropylphenyl)[(4-methylthiophenyl)methyl]amine (7.1 g) was obtained.
$^1$H-NMR(CDCl$_3$)δ: 1.19(6H, d, J=6.6 Hz), 2.47(3H, s), 2.80(1H, m), 3.87(1H, s), 4.36(2H, s), 6.57(2H, d, J=8.6 Hz), 7.04(2H, d, J=8.6 Hz), 7.23(2H, d, J=8.5 Hz), 7.29(2H, d, J=8.5 Hz).

Preparation Example 23

By the reaction and treatment in the same manner as in Preparation Example 1 using benzaldehyde (3.4 g) and 4-butylaniline (5 g) as starting materials, benzyl(4-butylphenyl)amine (2.7 g) was obtained.
$^1$H-NMR(CDCl$_3$)δ: 0.90(3H, t, J=7.3 Hz), 1.26–1.40(2H, m), 1.48–1.59(2H, m), 2.49(2H, t, J=8.1 Hz), 4.29(2H, s), 6.56(2H, d, J=8.6 Hz), 6.98(2H, d, J=8.6 Hz), 7.26–7.38(5H, m).

Preparation Example 24

By the reaction and treatment in the same manner as in Preparation Example 1 using 4-dimethylaminobenzaldehyde (1.5 g) and 3,4-dichloroaniline (1.6 g) as starting materials, (3,4-dichlorophenyl)[(4-dimethylaminophenyl)methyl]amine (1.8 g) was obtained. melting point: 117° C.

Preparation Example 25

By the reaction and treatment in the same manner as in Preparation Example 1 using 1H-indole-3-aldehyde (1.5 g) and 4-octylaniline (2.1 g) as starting materials, [(1H-indol-3-yl)methyl](4-octylphenyl)amine (1.8 g) was obtained.
$^1$H-NMR(CDCl$_3$)δ: 0.88(3H, t, J=6.6 Hz), 1.20–1.40(10H, m), 1.53–1.59(2H, m), 2.50(2H, t, J=8.1 Hz), 4.45(2H, s), 6.64(2H, d, J=8.6 Hz), 7.00(2H, d, J=8.6 Hz), 7.10–7.19(2H, m), 7.37(1H, d, J=8.0 Hz), 7.67(1H, d, J=8.0 Hz), 8.02(1H, s).

Preparation Example 26

By the reaction and treatment in the same manner as in Preparation Example 1 using 4-bromobenzaldehyde (1.9 g) and 4-isopropylaniline (1.4 g) as starting materials, [(4-bromophenyl)methyl](4-isopropylphenyl)amine (1.8 g) was obtained. melting point: 30° C.

Preparation Example 27

To a solution of 1-ethylpyrazole-4-carboxylic acid (2.34 g) in 1,2-dichloroethane (50 mL) were added thionyl chloride (1.83 mL) and several drops of dimethylformamide, and the mixture was stirred at 70° C. for 1.5 hr. The reaction mixture was concentrated under reduced pressure and methylene chloride (20 mL) was added to the residue. To this solution was added a solution of 4-isopropylaniline (2.29 mL) in methylene chloride (20 mL) under ice-cooling. The reaction mixture was heated to room temperature and stirred at the same temperature for 1 hr. The reaction mixture was poured into aqueous sodium hydrogencarbonate solution and extracted with chloroform. The organic layer was washed with saturated brine and dried over sodium sulfate. The solvent was evaporated and ether and hexane were added to the residue. The precipitated solid was collected by filtration to give 1-ethyl-N-(4-isopropylphenyl)pyrazole-4-carboxamide (3.76 g) (melting point: 141.0° C.). A 1N-borane-tetrahydrofuran complex/tetrahydrofuran solution (29 mL) was added to this compound (3.75 g) and the mixture was heated under reflux for 4 hr. The reaction mixture was cooled and 1N-hydrochloric acid (60 mL) was added. The mixture was stirred for one day at room temperature. The reaction mixture was poured into aqueous sodium hydrogencarbonate solution and the mixture was extracted with chloroform. The organic layer was washed with saturated brine and dried over sodium sulfate. The solvent was evaporated and the residue was purified by silica gel column chromatography to give (1-ethylpyrazol-4-ylmethyl)(4-isopropylphenyl)amine (1.95 g).

$^1$H-NMR(CDCl$_3$)δ: 1.21(6H, d, J=6.9 Hz), 1.47(3H, t, J=7.3 Hz), 2.81(1H, sept, J=6.9 Hz), 3.57–3.78(1H, brs), 4.14(2H, q, J=7.3 Hz), 4.15(2H, s), 6.62(2H, d, J=8.4 Hz), 7.06(2H, d, J=8.4 Hz), 7.36(1H, s), 7.47(1H, s)

Example 1

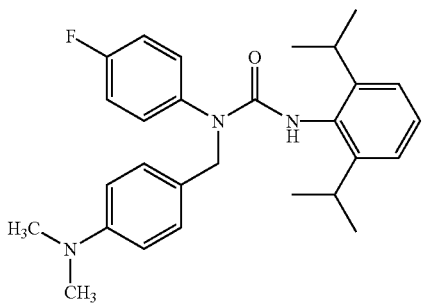

To a solution of [(4-dimethylaminophenyl)methyl](4-fluorophenyl)amine (0.52 g) in benzene (5 mL) was added 2,6-diisopropylphenyl isocyanate (0.46 mL) and the mixture was stirred at room temperature for 5 hr. The solvent was evaporated under reduced pressure and the residue was purified by silica gel column chromatography. The obtained crystals were subjected to recrystallization from a mixed solvent of diisopropyl ether and hexane to give N'-(2,6-diisopropylphenyl)-N-[(4-dimethylaminophenyl)methyl]-N-(4-fluorophenyl)urea (0.38 g). melting point: 124–125° C.

Example 2

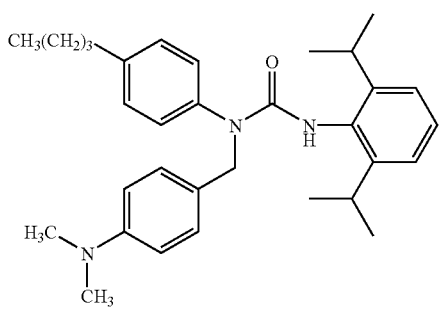

To a solution of (4-butylphenyl)[(4-dimethylaminophenyl)methyl]amine (0.6 g) in benzene (5 mL) was added 2,6-diisopropylphenyl isocyanate (0.46 mL) and the mixture was stirred overnight at room temperature. The solvent was evaporated under reduced pressure and the residue was purified by silica gel column chromatography to give N-(4-butylphenyl)-N'-(2,6-diisopropylphenyl)-N-[(4-dimethylaminophenyl)methyl]urea (0.34 g).

$^1$H-NMR(CDCl$_3$)δ: 0.92(3H, t, J=7.3 Hz), 1.16(12H, d, J=6.6 Hz), 1.20–1.50(2H, m), 1.52–1.70(2H, m), 2.59(2H, t, J=7.9 Hz), 2.93(6H, s), 3.00–3.20(2H, m), 4.79(2H, s), 5.41(1H, s), 6.65(2H, d, J=9.2 Hz), 7.00–7.22(9H, m).

Example 3

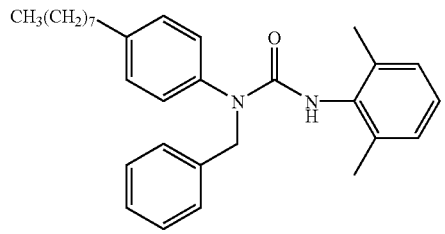

By the reaction and treatment in the same manner as in Example 2 using benzyl(4-octylphenyl)amine (1.0 g) and 2,6-dimethylphenyl isocyanate (6.4 mL) as starting materials, N-benzyl-N'-(2,6-dimethylphenyl)-N-(4-octylphenyl)urea (0.5 g) was obtained.

$^1$H-NMR(CDCl$_3$)δ: 0.86(3H, t, J=7.2 Hz), 1.25–1.30(10H, m), 1.56–1.61(2H, m), 1.68(2H, m), 2.21 (6H, s), 2.58(2H, t, J=7.9 Hz), 4.90(2H, s), 5.56(1H, s), 7.01(2H, s), 7.08(2H, d, J=7.9 Hz), 7.17(2H, d, J=7.9 Hz), 7.22–7.30(6H, m).

Example 4

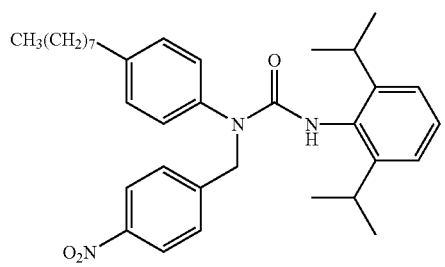

By the reaction and treatment in the same manner as in Example 2 using [(4-nitrophenyl)methyl](4-octylphenyl)amine (2.6 g) and 2,6-diisopropylphenyl isocyanate (1.55 g) as starting materials, N'-(2,6-diisopropylphenyl)-N-[(4-nitrophenyl)methyl]-N-(4-octylphenyl)urea (0.27 g) was obtained.

$^1$H-NMR(CDCl$_3$)δ: 0.87(3H, t, J=7.2 Hz), 1.17(12H, d, J=6.6 Hz), 1.25–1.30(10H, m), 1.68(2H, m), 2.58(2H, t, J=7.9 Hz), 3.08(2H, m), 4.98(2H, s), 5.56(1H, s), 7.09–7.13 (4H, m), 7.20–7.26(3H, m), 7.50(2H, d, J=8.6 Hz), 8.15(2H, d, J=8.6 Hz).

Example 5

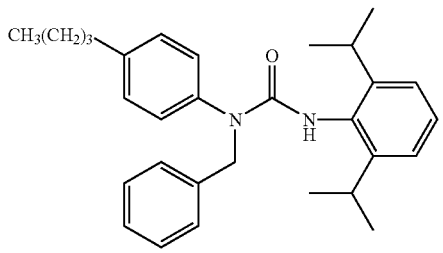

By the reaction and treatment in the same manner as in Example 2 using benzyl(4-butylphenyl)amine (1.0 g) and 2,6-diisopropylphenyl isocyanate (1.7 g) as starting materials, N-benzyl-N-(4-butylphenyl)-N'-(2,6-diisopropylphenyl)urea (0.51 g) was obtained.

$^1$H-NMR(CDCl$_3$)δ: 0.91(3H, t, J=7.3 Hz), 1.16(12H, d, J=6.6 Hz), 1.27–1.40(2H, m), 1.52–1.63(2H, m), 2.60(2H, t, J=7.9 Hz), 3.10(2H, m), 4.90(2H, s), 5.48(1H, s), 7.06–7.30 (12H, m).

Example 6

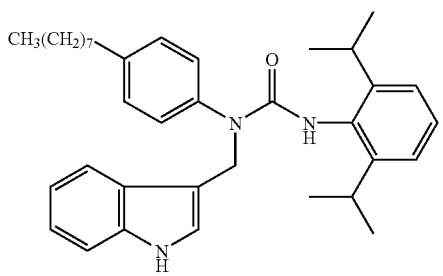

By the reaction and treatment in the same manner as in Example 2 using [(1H-indol-3-yl)methyl](4-octylphenyl)amine (0.61 g) and 2,6-diisopropylphenyl isocyanate (0.41 g) as starting materials, N'-(2,6-diisopropylphenyl)-N-[(1H-indol-3-yl)methyl]-N-(4-octylphenyl)urea (0.12 g) was obtained.

$^1$H-NMR(CDCl$_3$)δ: 0.87(3H, t, J=6.8 Hz), 1.14(6H, d, J=6.6 Hz), 1.22–1.41(10H, m), 1.55–1.60(2H, m), 2.56(2H, m), 3.09(2H, m), 5.09(2H, s), 6.90–7.40(12H, m).

Example 7

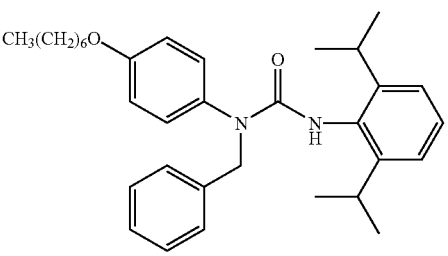

By the reaction and treatment in the same manner as in Example 2 using benzyl(4-heptyloxyphenyl)amine (2.1 g) and 2,6-diisopropylphenyl isocyanate (1.61 g) as starting materials, N-benzyl-N'-(2,6-diisopropylphenyl)-N-(4-heptyloxyphenyl)urea (1.4 g) was obtained.

$^1$H-NMR(CDCl$_3$)δ: 0.88(3H, t, J=7.3 Hz), 1.17(12H, d, J=6.6 Hz), 1.20–1.46(8H, m), 1.69–1.81(2H, m), 3.04–3.14 (2H, m), 3.94(2H, t, J=6.6 Hz), 4.86(2H, s), 5.47(1H, s), 6.86(2H, d, J=9.0 Hz), 7.03–7.30(10H, m).

Example 8

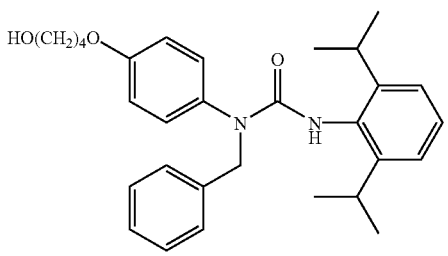

By the reaction and treatment in the same manner as in Example 2 using benzyl[4-(4-hydroxybutoxy)phenyl]amine (1.67 g) and 2,6-diisopropylphenyl isocyanate (1.37 g) as starting materials, 4-{4-[1-benzyl-3-(2,6-diisopropylphenyl)ureido]phenoxy}butanol (0.68 g) was obtained.

$^1$H-NMR(CDCl$_3$)δ: 1.16(12H, d, J=6.6 Hz), 1.55(1H, brs), 1.61–1.71(2H, m), 1.78–1.88(2H, m), 3.03–3.14(2H, m), 3.61(2H, m), 3.94(2H, t, J=6.6 Hz), 4.86(2H, s), 5.48 (1H, s), 6.84(2H, d, J=8.6 Hz), 7.18–7.30(10H, m).

Example 9

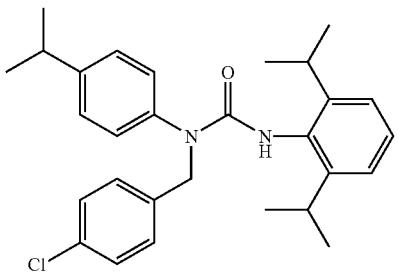

By the reaction and treatment in the same manner as in Example 2 using [(4-chlorophenyl)methyl](4-isopropylphenyl)amine (1.0 g) and 2,6-diisopropylphenyl isocyanate (0.9 g) as starting materials, N-[(4-chlorophenyl)methyl]-N'-(2,6-diisopropylphenyl)-N-(4-isopropylphenyl)urea (0.9 g) was obtained.

$^1$H-NMR(CDCl$_3$)δ: 1.17(12H, d, J=7.3 Hz), 1.24(6H, d, J=6.6 Hz), 2.83–2.99(1H, m), 3.01–3.15(2H, m), 4.84(2H, s), 5.49(1H, s), 7.07–7.12(4H, m), 7.21–7.28(7H, m).

Example 10

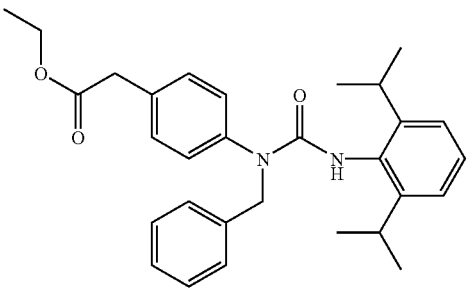

By the reaction and treatment in the same manner as in Example 2 using 2-(4-benzylaminophenyl)ethyl acetate (5.0 g) and 2,6-diisopropylphenyl isocyanate (5.7 g) as starting materials, 2-{4-[1-benzyl-3-(2,6-diisopropylphenyl)ureido]phenyl}ethyl acetate (1.39 g) was obtained.

$^1$H-NMR(CDCl$_3$)δ: 1.16(12H, d, J=6.6 Hz), 1.21(3H, t, J=7.3 Hz), 3.03–3.14(2H, m), 3.60(2H, s), 4.14(2H, q, J=7.3 Hz), 4.90(2H, s), 5.49(1H, s), 7.09–7.38(12H, m).

Example 11

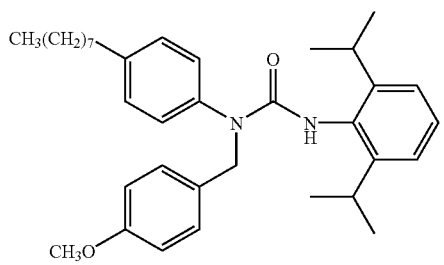

By the reaction and treatment in the same manner as in Example 2 using [(4-methoxyphenyl)methyl](4-octylphenyl)amine (2.2 g) and 2,6-diisopropylphenyl isocyanate (1.2 g) as starting materials, N'-(2,6-diisopropylphenyl)-N-[(4-methoxyphenyl)methyl]-N-(4-octylphenyl)urea (1.5 g) was obtained.

$^1$H-NMR(CDCl$_3$)δ: 0.87(3H, t, J=6.8 Hz), 1.16(12H, d, J=6.6 Hz), 1.22–1.41(10H, m), 1.53(2H, t, J=7.9 Hz), 2.56 (2H, t, J=7.9 Hz), 3.09(2H, m), 3.78(3H, s), 4.82(2H, s), 5.43(1H, s), 7.05(2H, d, J=8.0 Hz), 7.07–7.22(9H, m).

Example 12

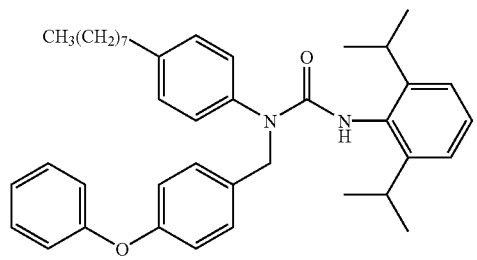

By the reaction and treatment in the same manner as in Example 2 using (4-octylphenyl)[(4-phenoxyphenyl)methyl]amine (1.53 g) and 2,6-diisopropylphenyl isocyanate (0.88 g) as starting materials, N'-(2,6-diisopropylphenyl)-N-(4-octylphenyl)-N-[(4-phenoxyphenyl)methyl]urea (0.55 g) was obtained.

$^1$H-NMR(CDCl$_3$)δ: 0.86(3H, t, J=6.6 Hz), 1.16(12H, d, J=6.6 Hz), 1.20–1.30(10H, m), 1.49–1.59(2H, m), 2.60(2H, t, J=8.8 Hz), 3.01–3.16(2H, m), 4.87(2H, s), 5.47(1H, s), 7.09–7.35(16H, m).

Example 13

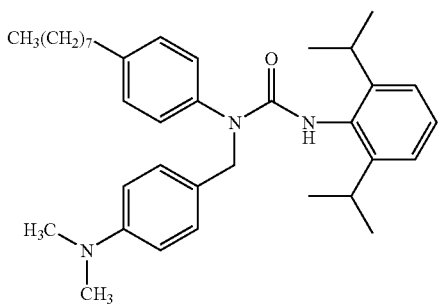

By the reaction and treatment in the same manner as in Example 2 using [(4-dimethylaminophenyl)methyl](4-octylphenyl)amine (1.1 g) and 2,6-diisopropylphenyl isocyanate (0.71 g) as starting materials, N'-(2,6-diisopropylphenyl)-N-[(4-dimethylaminophenyl)methyl]-N-(4-octylphenyl)urea (0.23 g) was obtained.

$^1$H-NMR(CDCl$_3$)δ: 0.85(3H, t, J=6.6 Hz), 1.16(12H, d, J=6.6 Hz), 1.22–1.41(10H, m), 1.58(2H, t, J=7.9 Hz), 2.58 (2H, t, J=8.0 Hz), 2.93(6H, s), 3.09(2H, m), 4.77(2H, s), 5.42(1H, s), 6.65(2H, d, J=8.6 Hz), 7.05–7.22(9H, m).

Example 14

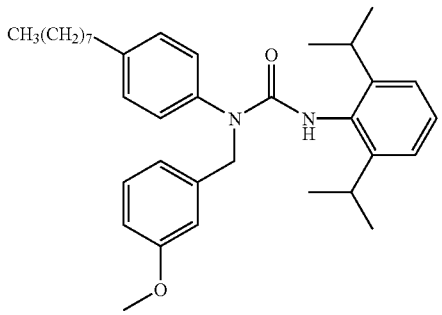

By the reaction and treatment in the same manner as in Example 2 using (3-methoxyphenylmethyl)(4-octylphenyl)amine (1.5 g) and 2,6-diisopropylphenyl isocyanate (1.12 g) as starting materials, N'-(2,6-diisopropylphenyl)-N-(3-methoxyphenylmethyl)-N-(4-octylphenyl)urea (0.46 g) was obtained.

$^1$H-NMR(CDCl$_3$)δ: 0.86(3H, t, J=6.6 Hz), 1.16(12H, d, J=6.6 Hz), 1.20–1.29(10H, m), 1.49–1.59(2H, m), 2.58(2H, t, J=8.6 Hz), 3.02–3.18(2H, m), 3.76(3H, s), 4.87(2H, s), 5.48(1H, s),6.60–6.85(2H, m), 6.93(1H, s), 7.09–7.38(8H, m).

Example 15

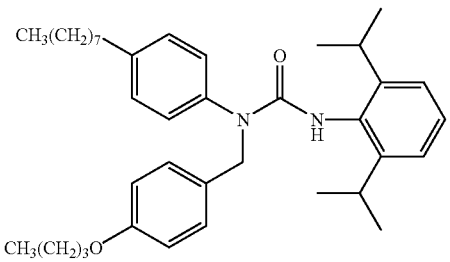

By the reaction and treatment in the same manner as in Example 2 using (4-butoxyphenylmethyl)(4-octylphenyl)amine (1.65 g) and 2,6-diisopropylphenyl isocyanate (1.05 g) as starting materials, N-(4-butoxyphenylmethyl)-N'-(2,6-diisopropylphenyl)-N-(4-octylphenyl)urea (0.92 g) was obtained.

$^1$H-NMR(CDCl$_3$)δ: 0.86(3H, t, J=6.6 Hz), 0.97(3H, t, J=7.3 Hz), 1.15(12H, d, J=6.6 Hz), 1.20–1.30(10H, m), 1.42–1.69(4H, m), 1.79–1.81(2H, m), 2.59(2H, t, J=7.9 Hz), 3.01–3.16(2H, m), 3.94(2H, t, J=6.0 Hz), 4.82(2H, s), 5.41(1H, s), 6.77(2H, dd, J=2.6, 9.2 Hz), 7.34–7.23(9H, m).

Example 16

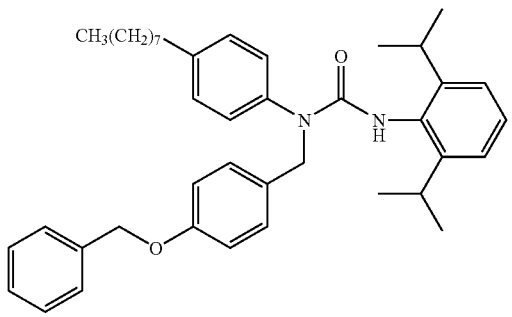

By the reaction and treatment in the same manner as in Example 2 using (4-benzyloxyphenylmethyl)(4-octylphenyl)amine (5.45 g) and 2,6-diisopropylphenyl isocyanate (3.14 g) as starting materials, N-(4-benzyloxyphenylmethyl)-N'-(2,6-diisopropylphenyl)-N-(4-octylphenyl)urea (0.56 g) was obtained.

$^1$H-NMR(CDCl$_3$)δ: 0.86(3H, t, J=6.6 Hz), 1.16(12H, d, J=6.6 Hz), 1.20–1.30(10H, m), 1.56–1.62(2H, m), 2.59(2H, t, J=7.9 Hz), 3.01–3.16(2H, m), 4.82(2H, S), 5.04(2H, s), 5.41(1H, s), 6.89(2H, d, J=8.6 Hz), 7.00–7.50(14H, m).

Example 17

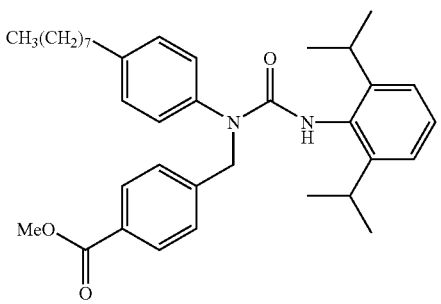

By the reaction and treatment in the same manner as in Example 2 using methyl 4-[(4-octylphenyl)aminomethyl]benzoate (2.65 g) and 2,6-diisopropylphenyl isocyanate (1.68 g) as starting materials, methyl 4-{[3-(2,6-diisopropylphenyl)-1-(4-octylphenyl)ureido]methyl}benzoate (0.29 g) was obtained.

$^1$H-NMR(CDCl$_3$)δ: 0.86(3H, t, J=6.6 Hz), 1.17(12H, d, J=6.6 Hz), 1.20–1.29(10H, m), 1.56–1.61(2H, m), 2.59(2H, t, J=7.9 Hz), 3.01–3.16(2H, m), 3.91(3H, s), 4.94(2H, s), 5.51(1H, s), 7.06–7.25(7H, m), 7.39(2H, d, J=7.9 Hz), 7.96(2H, d, J=7.9 Hz).

Example 18

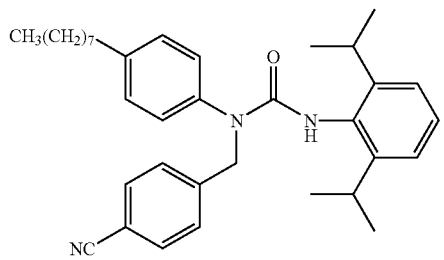

By the reaction and treatment in the same manner as in Example 2 using (4-cyanophenylmethyl)(4-octylphenyl)amine (3.65 g) and 2,6-diisopropylphenyl isocyanate (2.55 g) as starting materials, N-(4-cyanophenylmethyl)-N'-(2,6-diisopropylphenyl)-N-(4-octylphenyl)urea (0.49 g) was obtained.

$^1$H-NMR(CDCl$_3$)δ: 0.87(3H, t, J=6.6 Hz), 1.16(12H, d, J=6.6 Hz), 1.20–1.30(10H, m), 1.51–1.63(2H, m), 2.61(2H, t, J=7.9 Hz), 2.98–3.14(2H, m), 4.93(2H, s), 5.56(1H, s), 7.07–7.25(7H, m), 7.44(2H, d, J=7.9 Hz), 7.58(2H, d, J=7.9 Hz)

Example 19

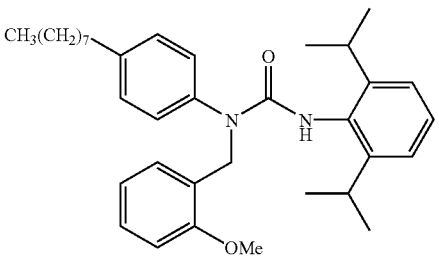

By the reaction and treatment in the same manner as in Example 2 using (2-methoxyphenylmethyl)(4-octylphenyl)amine (1.4 g) and 2,6-diisopropylphenyl isocyanate (0.96 g) as starting materials, N'-(2,6-diisopropylphenyl)-N-(2-methoxyphenylmethyl)-N-(4-octylphenyl)urea (1.36 g) was obtained.

$^1$H-NMR(CDCl$_3$)δ: 0.87(3H, t, J=6.6 Hz), 1.17(12H, d, J=6.6 Hz), 1.20–1.25(10H, m), 1.54–1.67(2H, m), 2.57(2H, t, J=7.9 Hz), 3.05–3.20(2H, m), 3.61(3H, s), 4.98(2H, s), 5.55(1H, s), 6.78(1H, d, J=8.8 Hz), 6.91(1H, t, J=7.9 Hz), 7.08–7.23(8H, m), 7.43(1H, dd, J=1.3, 7.2 Hz).

Example 20

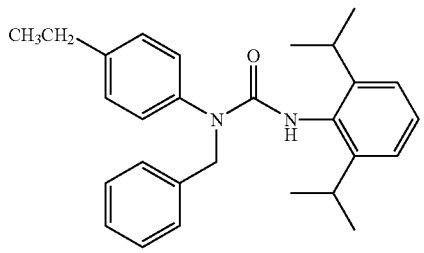

By the reaction and treatment in the same manner as in Example 2 using benzyl(4-ethylphenyl)amine (1.77 g) and 2,6-diisopropylphenyl isocyanate (1.96 g) as starting materials, N-benzyl-N'-(2,6-diisopropylphenyl)-N-(4-ethylphenyl)urea (1.49 g) was obtained.

$^1$H-NMR(CDCl$_3$)δ: 1.16–1.27(15H, m), 2.60(2H, q, J=7.3 Hz), 3.02–3.15(2H, m), 4.90(2H, s), 5.48(1H, s), 7.07–7.33(12H, m).

Example 21

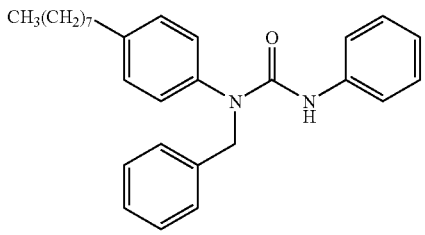

By the reaction and treatment in the same manner as in Example 2 using benzyl(4-octylphenyl)amine (2.0 g) and phenylisocyanate (0.91 mL) as starting materials, N-benzyl-N-(4-octylphenyl)-N'-phenylurea (1.9 g) was obtained.

$^1$H-NMR(CDCl$_3$)δ: 0.88(3H, t, J=7.2 Hz), 1.28–1.32(10H, m), 1.60(2H, m), 2.60(2H, t, J=7.9 Hz), 4.90(2H, s), 6.22(1H, s), 6.95–7.31(14H, m).

Example 22

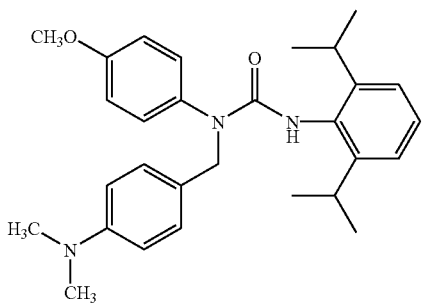

By the reaction and treatment in the same manner as in Example 2 using [(4-dimethylaminophenyl)methyl]](4-methoxyphenyl)amine (0.54 g) and 2,6-diisopropylphenyl isocyanate (0.46 mL) as starting materials, N'-(2,6-diisopropylphenyl)-N-[(4-dimethylaminophenyl)methyl]-N-(4-methoxyphenyl)urea (0.69 g) was obtained.

$^1$H-NMR(CDCl$_3$)δ: 1.16(12H, d, J=6.6 Hz), 2.93(6H, s), 3.00–3.20(2H, m), 3.79(3H, s), 4.77(2H, s), 5.40(1H, s), 6.65(2H, d, J=8.6 Hz), 6.80–7.30(9H, m).

Example 23

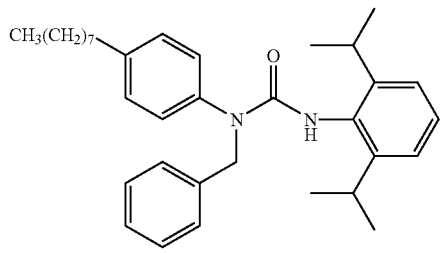

By the reaction and treatment in the same manner as in Example 2 using benzyl(4-octylphenyl)amine and 2,6-diisopropylphenyl isocyanate as starting materials, N-benzyl-N'-(2,6-diisopropylphenyl)-N-(4-octylphenyl)urea is obtained.

Example 24

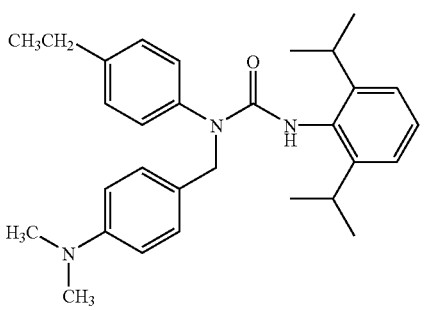

By the reaction and treatment in the same manner as in Example 2 using [(4-dimethylaminophenyl)methyl](4-ethylphenyl)amine (0.70 g) and 2,6-diisopropylphenyl isocyanate (0.68 g) as starting materials, N'-(2,6-diisopropylphenyl)-N-[(4-dimethylaminophenyl)methyl]-N-(4-ethylphenyl)urea (0.72 g) was obtained.

$^1$H-NMR(CDCl$_3$)δ: 1.16(12H, d, J=6.6 Hz), 1.25(3H, t, J=7.2 Hz), 2.64(2H, q, J=7.9 Hz), 2.93(6H, s), 3.09(2H, m), 4.78(2H, s), 5.42(1H, s), 6.66(2H, d, J=8.6 Hz), 6.86–7.22 (9H, m).

Example 25

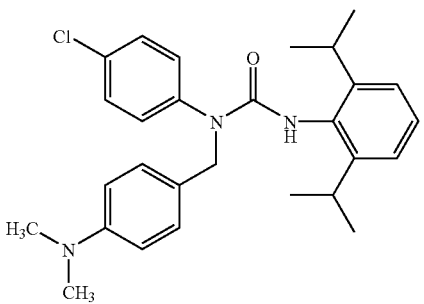

By the reaction and treatment in the same manner as in Example 1 using (4-chlorophenyl)[(4-dimethylaminophenyl)methyl]amine (0.70 g) and 2,6-diisopropylphenyl isocyanate (0.64 mL) as starting materials, N-(4-chlorophenyl)-N'-(2,6-diisopropylphenyl)-N-[(4-dimethylaminophenyl)methyl]urea (0.48 g) was obtained. melting point: 151–152° C.

Example 26

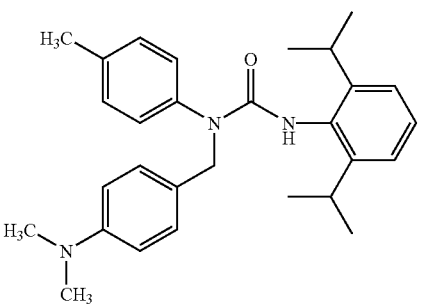

By the reaction and treatment in the same manner as in Example 1 using [(4-dimethylaminophenyl)methyl](4-methylphenyl)amine (0.70 g) and 2,6-diisopropylphenyl isocyanate (0.69 mL) as starting materials, N'-(2,6-diisopropylphenyl)-N-[(4-dimethylaminophenyl)methyl]-N-(4-methylphenyl)urea (0.41 g) was obtained. melting point: 124–125° C.

Example 27

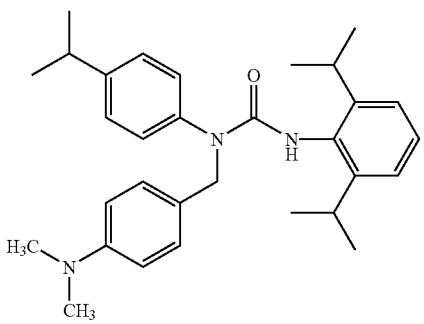

By the reaction and treatment in the same manner as in Example 2 using [(4-dimethylaminophenyl)methyl](4-isopropylphenyl)amine (0.80 g) and 2,6-diisopropylphenyl isocyanate (0.72 g) as starting materials, N'-(2,6-diisopropylphenyl)-N-[(4-dimethylaminophenyl)methyl]-N-(4-isopropylphenyl)urea (0.62 g) was obtained.
$^1$H-NMR(CDCl$_3$)δ: 1.16(12H, d, J=6.6 Hz), 1.23(6H, d, J=6.6 Hz), 2.94(6H, s), 3.04–3.14(2H, m), 3.44–3.51(1H, m), 4.79(2H, s), 5.42(1H, s), 6.66(2H, d, J=8.6 Hz), 7.07–7.23(9H, m).

Example 28

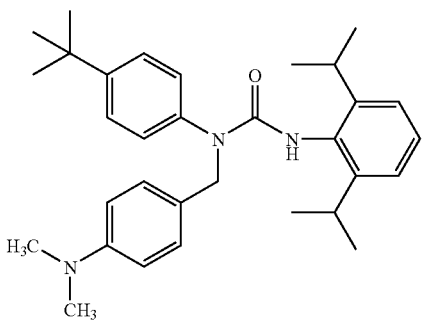

By the reaction and treatment in the same manner as in Example 1 using (4-tert-butylphenyl)[(4-dimethylaminophenyl)methyl]amine (0.7 g) and 2,6-diisopropylphenyl isocyanate (0.59 mL) as starting materials, N-(4-tert-butylphenyl)-N'-(2,6-diisopropylphenyl)-N-[(4-dimethylaminophenyl)methyl]urea (0.29 g) was obtained. melting point: 154–155° C.

Example 29

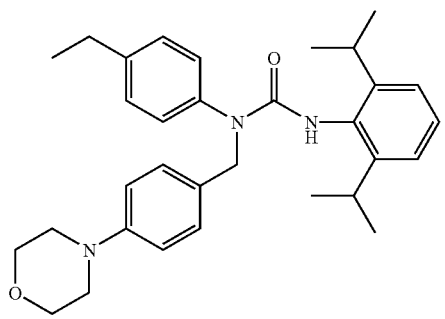

By the reaction and treatment in the same manner as in Example 1 using (4-ethylphenyl)(4-morpholinophenylmethyl)amine (0.63 g) and 2,6-diisopropylphenyl isocyanate (0.46 mL) as starting materials, N'-(2,6-diisopropylphenyl)-N-(4-ethylphenyl)-N-(4-morpholinophenylmethyl)urea (0.45 g) was obtained. melting point: 159–161° C.

Example 30

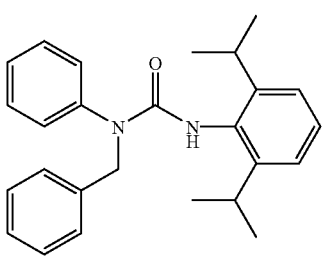

By the reaction and treatment in the same manner as in Example 2 using benzylphenylamine (1.3 g) and 2,6-diisopropylphenyl isocyanate (1.7 mL) as starting materials, N-benzyl-N'-(2,6-diisopropylphenyl)-N-phenylurea (1.8 g) was obtained.
$^1$H-NMR(CDCl$_3$)δ: 1.17(12H, d, J=7.2 Hz), 3.02–3.18 (2H, m), 4.92(2H, s), 5.45(1H, s), 7.09–7.42(13H, m).

Example 31

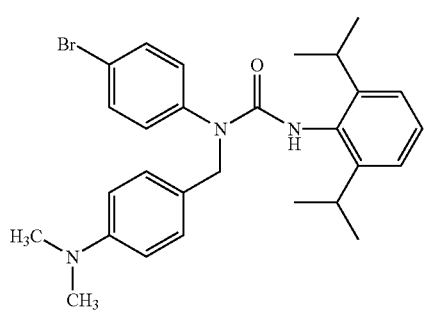

By the reaction and treatment in the same manner as in Example 1 using (4-bromophenyl)[(4-dimethylaminophenyl)methyl]amine (0.80 g) and 2,6-diisopropylphenyl isocyanate (0.62 mL) as starting materials, N-(4-bromophenyl)-N'-(2,6-diisopropylphenyl)-N-[(4-dimethylaminophenyl)methyl]urea (0.71 g) was obtained. melting point: 165–166° C.

Example 32

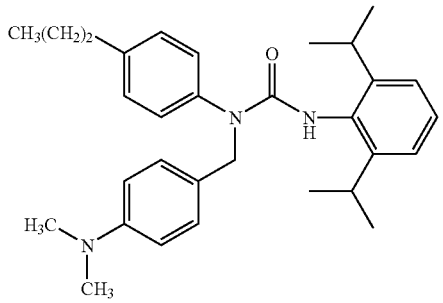

By the reaction and treatment in the same manner as in Example 2 using [(4-dimethylaminophenyl)methyl](4-propylphenyl)amine (0.80 g) and 2,6-diisopropylphenyl isocyanate (0.72 g) as starting materials, N'-(2,6-diisopropylphenyl)-N-[(4-dimethylaminophenyl)methyl]-N-(4-propylphenyl)urea (0.51 g) was obtained.

$^1$H-NMR(CDCl$_3$)δ: 0.92(3H, t, J=7.9 Hz), 1.16(12H, d, J=6.6 Hz), 1.58–1.67(2H, m), 2.57(2H, t, J=8.0 Hz), 2.93 (6H, s), 3.04–3.14(2H, m), 4.78(2H, s), 5.42(1H, s), 6.66 (2H, d, J=8.6 Hz), 6.86–7.22(9H, m).

Example 33

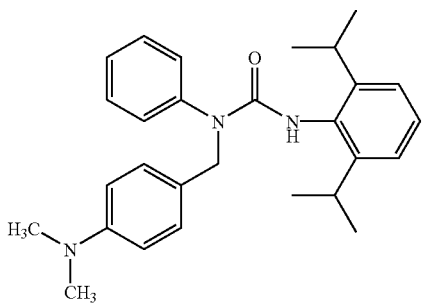

By the reaction and treatment in the same manner as in Example 2 using [(4-dimethylaminophenyl)methyl]phenylamine (0.70 g) and 2,6-diisopropylphenyl isocyanate (0.74 mL) as starting materials, N'-(2,6-diisopropylphenyl)-N-[(4-dimethylaminophenyl)methyl]-N-phenylurea (0.46 g) was obtained.

$^1$H-NMR(CDCl$_3$)δ: 1.15(12H, d, J=7.2 Hz), 2.93(6H, s), 3.05–3.15(2H, m), 4.81(2H, s), 5.40(1H, s), 6.65(2H, d, J=8.6 Hz), 7.08–7.20(7H, m), 7.30–7.76(3H, m).

Example 34

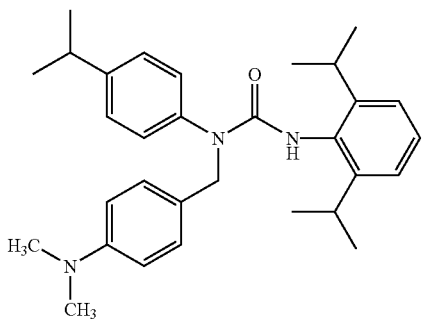

To a solution (50 mL) of N'-(2,6-diisopropylphenyl)-N-[(4-dimethylaminophenyl)methyl]-N-(4-isopropylphenyl)urea (6.7 g) in ethyl acetate was added a solution (30 mL) of fumaric acid (1.6 g) in methanol, and the obtained crystals were subjected to recrystallization from a mixed solvent of ethyl acetate and hexane to give N'-(2,6-diisopropylphenyl)-N-[(4-dimethylaminophenyl)methyl]-N-(4-isopropylphenyl)urea 9/10 fumarate (2.5 g). melting point: 203–206° C.

Example 35

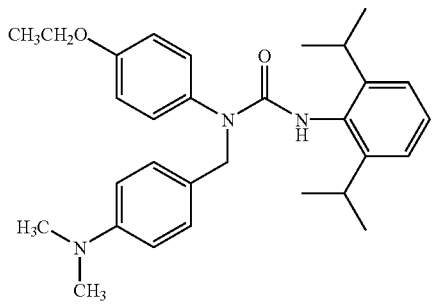

By the reaction and treatment in the same manner as in Example 2 using [(4-dimethylaminophenyl)methyl](4-ethoxyphenyl)amine (1.0 g) and 2,6-diisopropylphenyl isocyanate (0.89 g) as starting materials, N'-(2,6-diisopropylphenyl)-N-[(4-dimethylaminophenyl)methyl]-N-(4-ethoxyphenyl)urea (0.93 g) was obtained.

$^1$H-NMR(CDCl$_3$)δ: 1.16(12H, d, J=6.6 Hz), 1.40(3H, t, J=8.0 Hz), 2.93(6H, s), 3.03–3.18(2H, m), 4.02(2H, q, J=6.5 Hz), 4.75(2H, s), 5.40(1H, s), 6.66(2H, d, J=9.2 Hz), 6.86 (2H, d, J=9.2 Hz), 7.03–7.20(7H, m).

Example 36

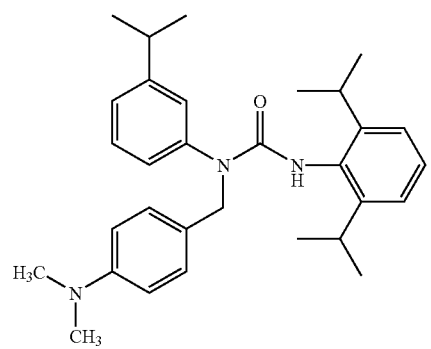

By the reaction and treatment in the same manner as in Example 2 using [(4-dimethylaminophenyl)methyl](3-isopropylphenyl)amine (1.0 g) and 2,6-diisopropylphenyl isocyanate (0.83 g) as starting materials, N'-(2,6-diisopropylphenyl)-N-[(4-dimethylaminophenyl)methyl]-N-(3-isopropylphenyl)urea (0.40 g) was obtained.

$^1$H-NMR(CDCl$_3$)δ: 1.16(6H, d, J=6.6 Hz), 1.17(12H, d, J=6.6 Hz), 2.81–2.89(1H, m), 2.92(6H, s), 3.00–3.30(2H, m), 4.80(2H, s), 5.40(1H, s), 6.65(2H, d, J=9.3 Hz), 6.96–7.31(9H, m).

Example 37

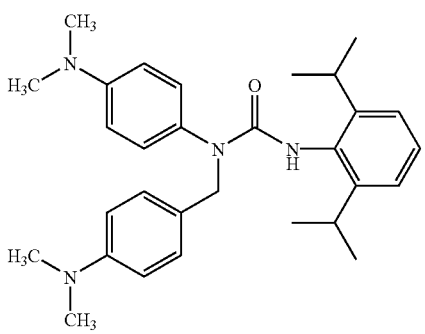

By the reaction and treatment in the same manner as in Example 2 using (4-dimethylaminophenyl)[(4-dimethylaminophenyl)methyl]amine (1.05 g) and 2,6-diisopropylphenyl isocyanate (1.03 g) as starting materials, N'-(2,6-diisopropylphenyl)-N-(4-dimethylaminophenyl)-N-[(4-dimethylaminophenyl)methyl]urea (0.815 g) was obtained.

$^1$H-NMR(CDCl$_3$)δ: 1.16(12H, d, J=6.6 Hz), 2.93(6H, s), 2.94(6H, s), 3.01–3.19(2H, m), 4.75(2H, s), 5.48(1H, s), 6.65(4H, d, J=8.3 Hz), 6.98(2H, dd, J=2.0, 6.6 Hz), 7.14–7.21(5H, m).

Example 38

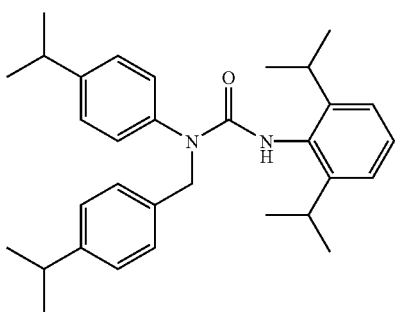

By the reaction and treatment in the same manner as in Example 2 using (4-isopropylphenyl)[(4-isopropylphenyl)methyl]amine (1.0 g) and 2,6-diisopropylphenyl isocyanate (0.99 g) as starting materials, N'-(2,6-diisopropylphenyl)-N-(4-isopropylphenyl)-N-[(4-isopropylphenyl)methyl]urea (0.37 g) was obtained.

$^1$H-NMR(CDCl$_3$)δ: 1.16(12H, d, J=6.6 Hz), 1.23(6H, d, J=6.6 Hz), 1.25(6H, d, J=6.6 Hz), 2.89(2H, m), 3.10(2H, m), 4.86(2H, s), 5.48(1H, s), 7.08–7.25(11H, m).

Example 39

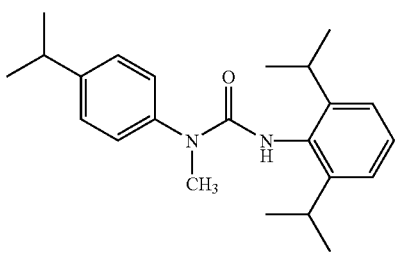

By the reaction and treatment in the same manner as in Example 2 using (4-isopropylphenyl)methylamine (1.13 g) and 2,6-diisopropylphenyl isocyanate (2.15 g) as starting materials, N'-(2,6-diisopropylphenyl)-N-(4-isopropylphenyl)-N-methylurea (0.57 g) was obtained.

$^1$H-NMR(CDCl$_3$)δ: 1.16(12H, d, J=6.6 Hz), 1.27(6H, d, J=6.6 Hz), 2.87–3.01(1H, m), 3.04–3.27(2H, m), 3.32(3H, s), 5.51(1H, s), 7.10(2H, d, J=7.3 Hz), 7.18(1H, d, J=6.6 Hz), 7.33(4H, s).

Example 40

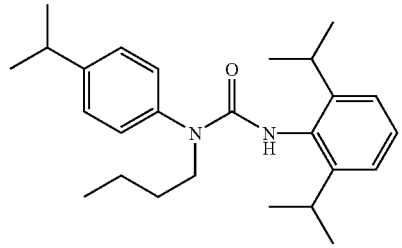

By the reaction and treatment in the same manner as in Example 2 using butyl(4-isopropylphenyl)amine (1.8 g) and 2,6-diisopropylphenyl isocyanate (2.7 g) as starting materials, N-butyl-N'-(2,6-diisopropylphenyl)-N-(4-isopropylphenyl)urea (1.3 g) was obtained.

$^1$H-NMR(CDCl$_3$)δ: 0.91(3H, t, J=7.2 Hz), 1.16(12H, d, J=6.6 Hz), 1.27(6H, d, J=7.2 Hz), 1.30–1.60(4H, m), 2.87–3.01(1H, m), 3.04–3.27(2H, m), 3.72(2H, t, J=7.3 Hz), 5.38(1H, s), 7.05(2H, d, J=8.6 Hz), 7.19–7.35(7H, m).

Example 41

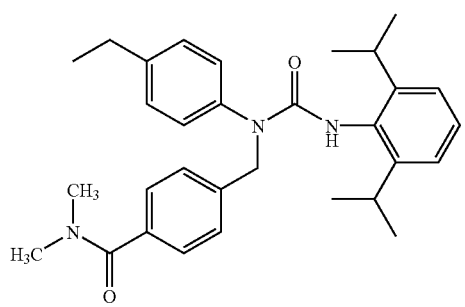

By the reaction and treatment in the same manner as in Example 1 using N,N-dimethyl-4-[(4-ethylphenyl)aminomethyl]benzamide (0.6 g) and 2,6-diisopropylphenyl isocyanate (0.46 mL) as starting materials, 4-[3-(2,6-diisopropylphenyl)-1-(4-ethylphenyl)ureidomethyl]-N,N-dimethylbenzamide (0.34 g) was obtained. melting point: 170–172° C.

Example 42

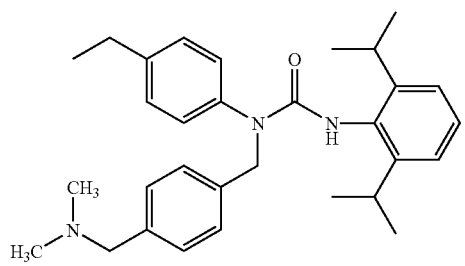

By the reaction and treatment in the same manner as in Example 2 using {[4-(dimethylaminomethyl)phenyl]methyl}(4-ethylphenyl)amine (0.51 g) and 2,6-diisopropylphenyl isocyanate (0.42 mL) as starting materials, which was followed by addition of oxalic acid and recrystallization from ethyl acetate, N'-(2,6-diisopropylphenyl)-N-{[4-(dimethylaminomethyl)phenyl]methyl}-N-(4-ethylphenyl)urea 1 oxalate (0.21 g) was obtained. melting point: 145–146° C.

Example 43

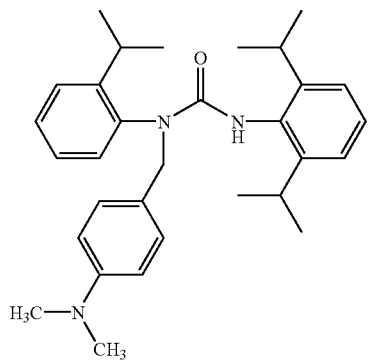

By the reaction and treatment in the same manner as in Example 2 using [(4-dimethylaminophenyl)methyl](2-isopropylphenyl)amine (1.6 g) and 2,6-diisopropylphenyl isocyanate (1.7 g) as starting materials, N'-(2,6-diisopropylphenyl)-N-[(4-dimethylaminophenyl)methyl]-N-(2-isopropylphenyl)urea (0.24 g) was obtained.

$^1$H-NMR(CDCl$_3$)δ: 1.15(12H, d, J=6.6 Hz), 1.22(3H, d, J=6.6 Hz), 1.29(3H, d, J=6.6 Hz), 2.93(6H, s), 3.09–3.14 (2H, m), 3.33–3.49(1H, m), 3.96(1H, d, J=14 Hz), 5.30(1H, s), 5.49(1H, d, J=14 Hz), 6.62(2H, dd, J=2.0, 6.6 Hz), 6.77(1H, dd, J=1.3, 6.6 Hz), 7.08–7.44(8H, m).

Example 44

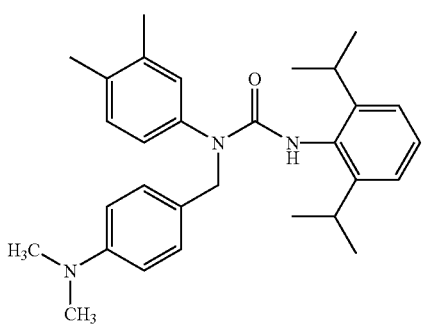

By the reaction and treatment in the same manner as in Example 2 using [(4-dimethylaminophenyl)methyl](3,4-dimethylphenyl)amine (1.4 g) and 2,6-diisopropylphenyl isocyanate (1.5 g) as starting materials, N'-(2,6-diisopropylphenyl)-N-[(4-dimethylaminophenyl)methyl]-N-(3,4-dimethylphenyl)urea (0.77 g) was obtained.

$^1$H-NMR(CDCl$_3$)δ: 1.16(12H, d, J=6.6 Hz), 2.22(3H, s), 2.24(3H, s), 2.93(6H, s), 3.05–3.20(2H, m), 4.78(2H, s), 5.45(1H, s), 6.66(2H, d, J=8.6 Hz), 6.86(1H, dd, J=2.6, 8.0 Hz), 6.98(1H, d, J=2.0 Hz), 7.08–7.20(6H, m)

Example 45

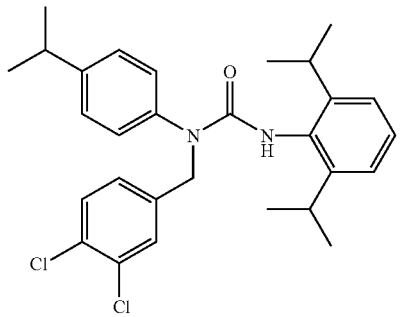

By the reaction and treatment in the same manner as in Example 2 using [(3,4-dichlorophenyl)methyl](4-isopropylphenyl)amine (2.5 g) and 2,6-diisopropylphenyl isocyanate (2.7 g) as starting materials, N-(3,4-dichlorophenylmethyl)-N'-(2,6-diisopropylphenyl)-N-(4-isopropylphenyl)urea (1.2 g) was obtained.

$^1$H-NMR(CDCl$_3$)δ: 1.19(12H, d, J=7.4 Hz), 1.24(6H, d, J=6.6 Hz), 2.92(1H, m), 3.08(2H, m), 4.83(2H, s), 5.51(1H, s), 7.09–7.29(8H, m), 7.35(1H, d, J=8.5 Hz), 7.47(1H, d, J=2.0 Hz).

Example 46

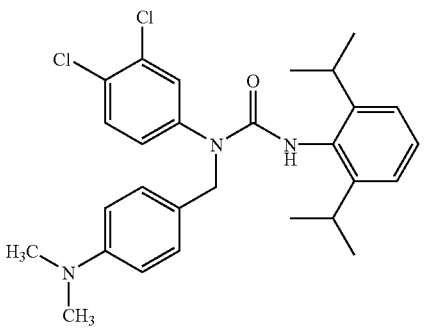

By the reaction and treatment in the same manner as in Example 1 using (3,4-dichlorophenyl)[4-(dimethylaminophenyl)methyl]amine (1.8 g) and 2,6-diisopropylphenyl isocyanate (1.6 g) as starting materials, N-(3,4-dichlorophenyl)-N'-(2,6-diisopropylphenyl)-N-[4-(dimethylaminophenyl)methyl]urea (0.82 g) was obtained. melting point: 119–121° C.

Example 47

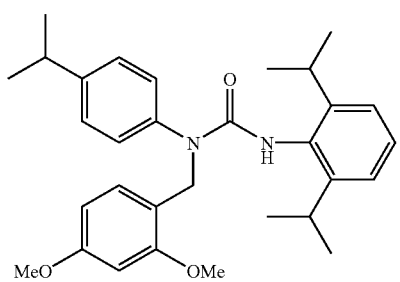

By the reaction and treatment in the same manner as in Example 2 using [(2,4-dimethoxyphenyl)methyl](4-isopropylphenyl)amine (1.0 g) and 2,6-diisopropylphenyl isocyanate (1.2 g) as starting materials, N'-(2,6-diisopropylphenyl)-N-[(2,4-dimethoxyphenyl)methyl]-N-(4-isopropylphenyl)urea (1.6 g) was obtained.

$^1$H-NMR(CDCl$_3$)δ: 1.16(12H, d, J=7.4 Hz), 1.22(6H, d, J=6.6 Hz), 2.81–2.91(1H, m), 3.05–3.17(2H, m), 3.54(3H, s), 3.79(3H, s), 4.90(2H, s), 5.50(1H, s), 6.35(1H, d, J=2.0 Hz), 6.45(1H, d, J=8.0 Hz), 7.08–7.34(8H, m).

Example 48

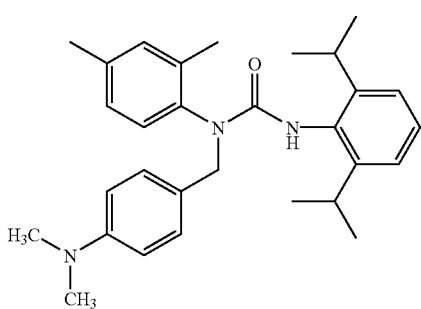

By the reaction and treatment in the same manner as in Example 1 using [(4-dimethylaminophenyl)methyl](2,4-dimethylphenyl)amine (1.0 g) and 2,6-diisopropylphenyl isocyanate (1.2 g) as starting materials, N'-(2,6-diisopropylphenyl)-N-[(4-dimethylaminophenyl)methyl]-N-(2,4-dimethylphenyl)urea (0.78 g) was obtained. melting point: 100° C.

Example 49

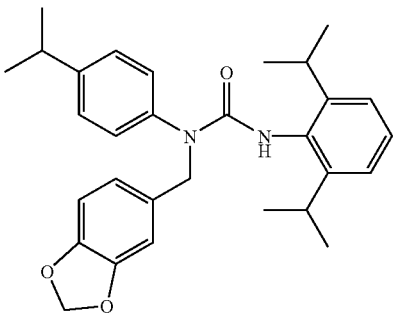

By the reaction and treatment in the same manner as in Example 2 using (benzo[d]1,3-dioxolen-5-ylmethyl)(4-isopropylphenyl)amine and 2,6-diisopropylphenyl isocyanate (1.2 g) as starting materials, N-(benzo[d]1,3-dioxolen,-5-ylmethyl)-N'-(2,6-diisopropylphenyl)-N-(4-isopropylphenyl)urea (1.0 g) was obtained.

$^1$H-NMR(CDCl$_3$)δ: 1.18(12H, d, J=7.4 Hz), 1.24(6H, d, J=6.6 Hz), 2.81–2.99(1H, m), 3.03–3.17(2H, m), 4.79(2H, s), 5.46(1H, s), 5.94(2H, s), 6.68(2H, d, J=1.3 Hz), 6.91(1H, s), 7.09–7.25(7H, m).

Example 50

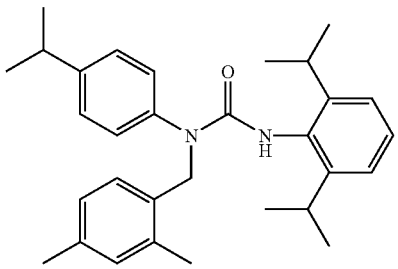

By the reaction and treatment in the same manner as in Example 1 using [(2,4-dimethylphenyl)methyl](4-isopropylphenyl)amine (2.2 g) and 2,6-diisopropylphenyl isocyanate (2.7 g) as starting materials, N'-(2,6-diisopropylphenyl)-N-[(2,4-dimethylphenyl)methyl]-N-(4-isopropylphenyl)urea (0.56 g) was obtained. melting point: 100° C.

Example 51

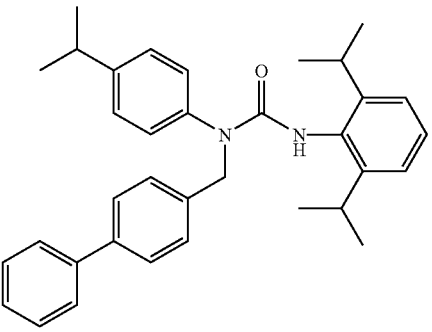

By the reaction and treatment in the same manner as in Example 2 using (4-biphenylylmethyl)(4-isopropylphenyl)amine (1.0 g) and 2,6-diisopropylphenyl isocyanate (0.88 g) as starting materials, N-(4-biphenylylmethyl)-N'-(2,6-diisopropylphenyl)-N-(4-isopropylphenyl)urea (0.88 g) was obtained.

$^1$H-NMR(CDCl$_3$)δ: 1.18(12H, d, J=6.6 Hz), 1.24(6H, d, J=6.6 Hz) 2.91(1H, m), 3.11(2H, m), 4.93(2H, s), 5.51(1H, s), 7.10–7.62(16H, m).

Example 52

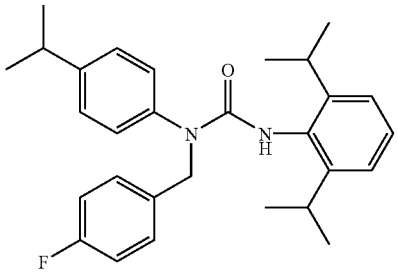

By the reaction and treatment in the same manner as in Example 1 using [(4-fluorophenyl)methyl](4-isopropylphenyl)amine (2.2 g) and 2,6-diisopropylphenyl isocyanate (2.2 g) as starting materials, N'-(2,6-diisopropylphenyl)-N-[(4-fluorophenyl)methyl]-N-(4-isopropylphenyl)urea (0.82 g) was obtained. melting point: 80° C.

Example 53

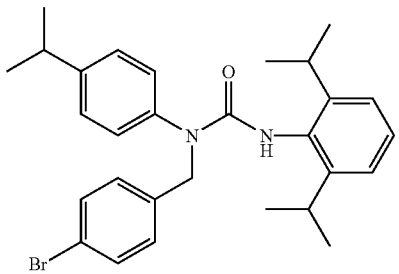

By the reaction and treatment in the same manner as in Example 2 using [(4-bromophenyl)methyl](4-isopropylphenyl)amine (2.7 g) and 2,6-diisopropylphenyl isocyanate (2.1 g) as starting materials, N-[(4-bromophenyl)methyl]-N'-(2,6-diisopropylphenyl)-N-(4-isopropylphenyl)urea (1.2 g) was obtained.

$^1$H-NMR(CDCl$_3$)δ: 1.16(12H, d, J=7.3 Hz), 1.24(6H, d, J=6.6 Hz), 2.85–2.95(1H, m), 3.00–3.15(2H, m), 4.82(2H, s), 5.48(1H, s), 7.05–7.13(4H, m), 7.18–7.30(5H, m), 7.35–7.45(2H, m).

Example 54

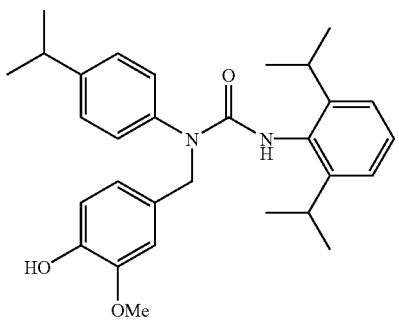

By the reaction and treatment in the same manner as in Example 2 using (4-hydroxy-3-methoxyphenylmethyl)(4-isopropylphenyl)amine (7.0 g) and 2,6-diisopropylphenyl isocyanate (5.5 mL) as starting materials, N'-(2,6-diisopropylphenyl)-N-[(4-hydroxy-3-methoxyphenyl)methyl]-N-(4-isopropylphenyl)urea (0.65 g) was obtained.

$^1$H-NMR(CDCl$_3$)δ: 1.16(12H, d, J=7.2 Hz), 1.23(6H, d, J=6.6 Hz), 2.86–3.00(1H, m), 3.03–3.31(2H, m), 3.82(3H, s), 4.78(2H, s), 5.41(1H, s), 6.55–6.68(1H, m), 6.70–6.80(1H, m), 7.01–7.26(8H, m).

Example 55

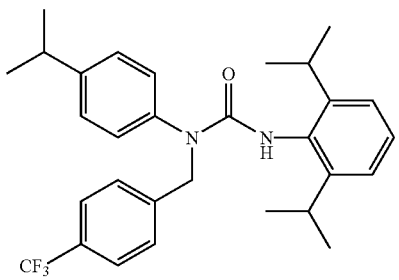

By the reaction and treatment in the same manner as in Example 2 using (4-isopropylphenyl)[(4-trifluoromethylphenyl)methyl]amine (2.4 g) and 2,6-diisopropylphenyl isocyanate (2.1 g) as starting materials, N'-(2,6-diisopropylphenyl)-N-(4-isopropylphenyl)-N-[(4-trifluoromethylphenyl)methyl]urea (1.4 g) was obtained.

$^1$H-NMR(CDCl$_3$)δ: 1.17(12H, d, J=6.4 Hz), 1.24(6H, d, J=6.5 Hz), 2.89–2.98(1H, m), 3.05–3.18(2H, m), 4.94(2H, s), 5.52(1H, s), 7.05–7.30(7H, m), 7.45(2H, d, J=7.9 Hz), 7.55(2H, d, J=7.9 Hz).

Example 56

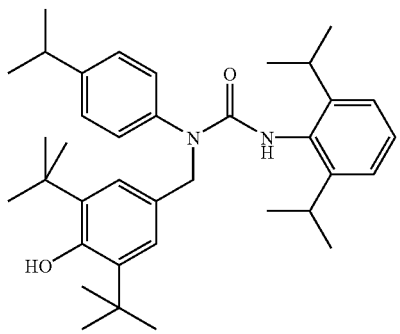

By the reaction and treatment in the same manner as in Example 2 using (3,5-di-tert-butyl-4-hydroxyphenylmethyl)(4-isopropylphenyl)amine (2.0 g) and 2,6-diisopropylphenyl isocyanate (1.8 mL) as starting materials, N-(3,5-di-tert-butyl-4-hydroxyphenylmethyl)-N'-(2,6-diisopropylphenyl)-N-(4-isopropylphenyl)urea (0.82 g) was obtained.

$^1$H-NMR(CDCl$_3$)δ: 1.15(12H, d, J=7.3 Hz), 1.23(6H, d, J=7.3 Hz), 1.38(18H, s), 2.85–2.98(1H, m), 3.00–3.16(2H, m), 4.80(2H, s), 5.11(1H, s), 5.44(1H, s), 6.99–7.26(9H, m).

Example 57

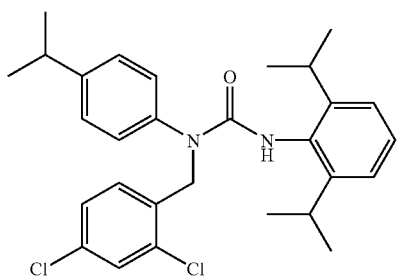

By the reaction and treatment in the same manner as in Example 2 using [(2,4-dichlorophenyl)methyl](4-isopropylphenyl)amine (2.7 g) and 2,6-diisopropylphenyl isocyanate (2.1 g) as starting materials, N-[(2,4-dichlorophenyl)methyl]-N'-(2,6-diisopropylphenyl)-N-(4-isopropylphenyl)urea (0.43 g) was obtained.

$^1$H-NMR(CDCl$_3$)δ: 1.17(12H, d, J=6.6 Hz), 1.23(6H, d, J=6.6 Hz), 2.85–3.00(1H, m), 3.00–3.20(2H, m), 5.03(2H, s), 5.58(1H, s), 7.10–7.31(9H, m), 7.50(1H, d, J=7.9 Hz).

Example 58

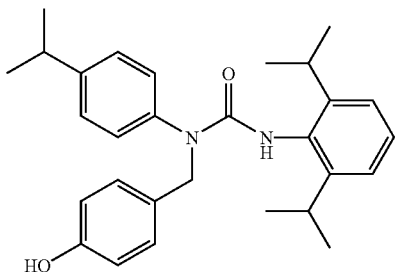

A solution of N-[(4-benzyloxyphenyl)methyl]-N'-(2,6-diisopropylphenyl)-N-(4-isopropylphenyl)urea (5.23 g), 10% Pd—C (0.6 g) and ammonium formate (3.1 g) in methanol was stirred at room temperature for 5 hr. Pd—C was filtered off from the reaction system and the filtrate was concentrated and the residue was purified by silica gel column chromatography to give N'-(2,6-diisopropylphenyl)-N-[(4-hydroxyphenyl)methyl]-N-(4-isopropylphenyl)urea (0.78 g).

$^1$H-NMR(CDCl$_3$)δ: 1.15(12H, d, J=7.3 Hz), 1.24(6H, d, J=7.3 Hz), 2.85–2.93(1H, m), 3.04–3.12(2H, m), 4.79(2H, s), 5.46(1H, s), 5.92(1H, s), 6.64(2H, d, J=8.6 Hz), 7.05–7.30(9H, m).

Example 59

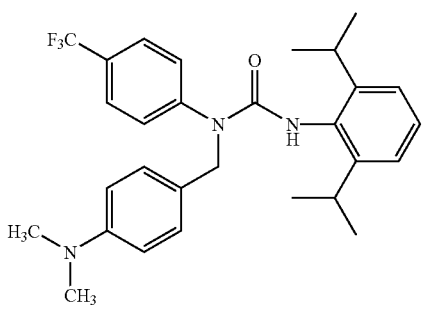

By the reaction and treatment in the same manner as in Example 1 using [(4-dimethylaminophenyl)methyl](4-trifluoromethylphenyl)amine (1.0 g) and 2,6-diisopropylphenyl isocyanate (0.83 g) as starting materials, N'-(2,6-diisopropylphenyl)-N-[(4-dimethylaminophenyl)methyl]-N-(4-trifluoromethylphenyl)urea (0.23 g) was obtained. melting point: 129–130° C.

Example 60

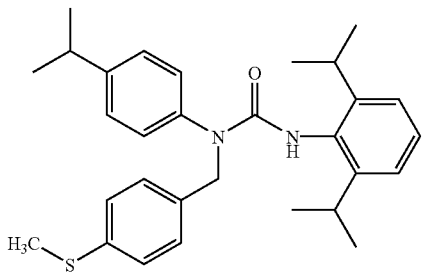

By the reaction and treatment in the same manner as in Example 2 using (4-isopropylphenyl)[(4-methylthiophenyl)methyl]amine (2.0 g) and 2,6-diisopropylphenyl isocyanate (2.1 g) as starting materials, N'-(2,6-diisopropylphenyl)-N-(4-isopropylphenyl)-N-[(4-methylthiophenyl)methyl]urea (2.9 g) was obtained.

$^1$H-NMR(CDCl$_3$)δ: 1.16(12H, d, J=7.3 Hz), 1.23(6H, d, J=7.3 Hz), 2.48(3H, s), 2.80–2.98(1H, m), 3.01–3.15(2H, m), 4.84(2H, s), 5.46(1H, s), 7.08–7.26(11H, m).

Example 61

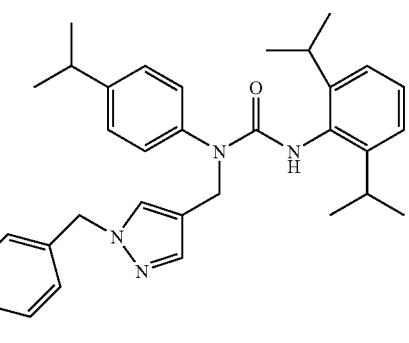

To a solution of (4-isopropylphenyl){[1-(4-trifluoromethylbenzyl)pyrazol-4-yl]methyl}amine (1.17 g) in toluene (20 mL) was added 2,6-diisopropylphenyl isocyanate (1 mL) and the mixture was stirred overnight at room temperature. The reaction mixture was washed with saturated brine, dried over magnesium sulfate, evaporated under reduced pressure, and the residue was purified by silica gel column chromatography. The obtained crystals were subjected to recrystallization from a mixed solvent of diisopropyl ether and ethyl acetate to give, N'-(2,6-diisopropylphenyl)-N-(4-isopropylphenyl)-N-{[1-(4-trifluoromethylbenzyl)pyrazol-4-yl]methyl}urea (1.23 g). melting point: 134–135° C.

Example 62

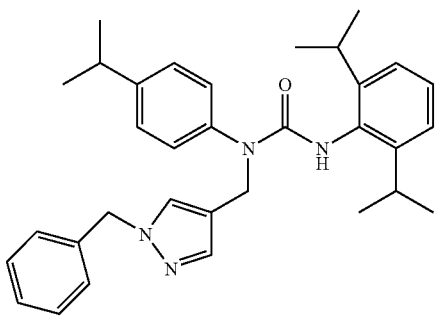

To a solution of [(1-benzylpyrazol-4-yl)methyl](4-isopropylphenyl)amine (0.17 g) in toluene (5 mL) was added 2,6-diisopropylphenyl isocyanate (0.12 mL) and the mixture was stirred overnight at room temperature. The reaction mixture was washed with saturated brine and dried over magnesium sulfate. The solvent was evaporated under reduced pressure and the residue was purified by silica gel column chromatography to give N-[(1-benzylpyrazol-4-yl)methyl]-N'-(2,6-diisopropylphenyl)-N-(isopropylphenyl)urea (0.24 g).

$^1$H-NMR(CDCl$_3$)δ: 1.12(12H, d, J=6.8 Hz), 1.25(6H, d, J=6.9 Hz), 2.88–3.06(3H, m), 4.67(2H, s), 5.25(2H, s), 5.39(1H, s), 7.08–7.31(12H, m), 7.41–7.43(2H, m)

Example 63

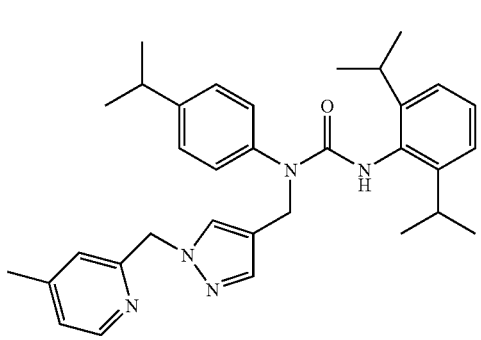

In the same manner as in Example 62, reaction and treatment were conducted using (4-isopropylphenyl)({1-[(4-methyl-2-pyridyl)methyl]pyrazol-4-yl}methyl)amine (0.42 g) and 2,6-diisopropylphenyl isocyanate (0.42 mL) as starting materials. Further, the obtained oil compound was converted to hydrochloride with 4N hydrochloric acid-ethyl acetate to give N'-(2,6-diisopropylphenyl)-N-(4-isopropylphenyl)-N-({1-[(4-methyl-2-pyridyl)methyl]pyrazol-4-yl}methyl)urea hydrochloride (0.33 g).

$^1$H-NMR(DMSO-$d_6$)δ: 1.08(12H, d, J=6.9 Hz), 1.20(6H, d, J=6.9 Hz), 2.51(3H, s), 2.85–2.94(1H, m), 3.02–3.11(2H, m), 4.67(2H, s), 5.72(2H, s), 7.07–7.09(3H, m), 7.16–7.19 (3H, m), 7.27–7.30(3H, m), 7.42(1H, s), 7.77(1H, d, J=5.6 Hz), 7.83(1H, s), 8.74(1H, d, J=5.9 Hz)

Example 64

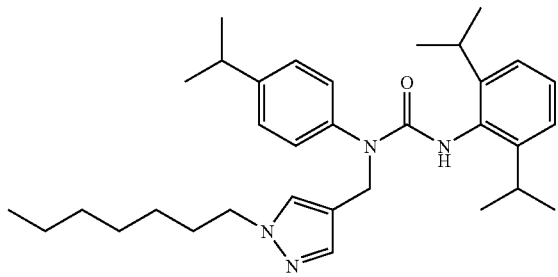

By the reaction and treatment in the same manner as in Example 62 using [(1-heptylpyrazol-4-yl)methyl](4-isopropylphenyl)amine (1.1 g) and 2,6-diisopropylphenyl isocyanate (1.13 mL) as starting materials, N'-(2,6-diisopropylphenyl)-N-[(1-heptylpyrazol-4-yl)methyl]-N-(4-isopropylphenyl)urea (1.35 g) was obtained.

$^1$H-NMR(CDCl$_3$)δ: 0.88(3H, t, J=6.7 Hz), 1.15(12H, d, J=6.6 Hz), 1.24–1.28(14H, m), 1.77–1.78(2H, m), 2.88–2.98 (1H, m), 3.00–3.09(2H, m), 4.04(2H, t, J=7.1 Hz), 4.67(2H, s), 5.42(1H, s), 7.09–7.21(5H, m), 7.27(2H, d, J=8.2 Hz), 7.35(1H, s), 7.43(1H, s)

Example 65

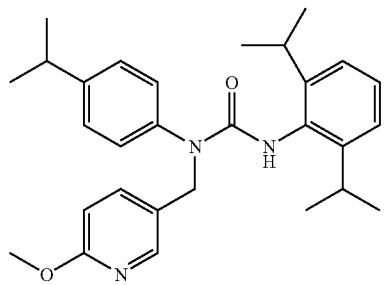

By the reaction and treatment in the same manner as in Example 62 using (4-isopropylphenyl)[(2-methoxy-5-pyridyl)methyl]amine (0.50 g) and 2,6-diisopropylphenyl isocyanate (0.63 mL) as starting materials, N'-(2,6-diisopropylphenyl)-N-(4-isopropylphenyl)-N-[(2-methoxy-5-pyridyl)methyl]urea (0.57 g) was obtained.

$^1$H-NMR(CDCl$_3$)δ: 1.16(12H, d, J=6.7 Hz), 1.24(6H, d, J=6.9 Hz), 2.87–2.96(1H, m), 3.00–3.09(2H, m), 3.92(3H, s), 4.81(2H, s), 5.45(1H, s), 6.71(1H, d, J=8.3 Hz), 7.06–7.12(4H, m), 7.22–7.27(3H, m), 7.73–7.88(1H, m), 7.88(1H, s)

Example 66

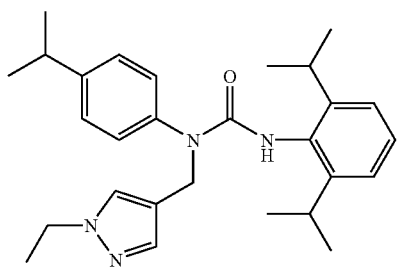

By the reaction and treatment in the same manner as in Example 2 using (1-ethylpyrazol-4-ylmethyl)(4-isopropylphenyl)amine (365 mg) and 2,6-diisopropylisocyanate (305 mg) as starting materials, N'-(2,6-diisopropylphenyl)-N-(1-ethylpyrazol-4-ylmethyl)-N-(4-isopropylphenyl)urea (530 mg) was obtained.

$^1$H-NMR(CDCl$_3$)δ: 1.14(12H, d, J=6.9 Hz), 1.26(6H, d, J=6.9 Hz), 1.45(3H, t, J=7.3 Hz), 2.94(1H, sept, J=6.9 Hz), 3.04(2H, sept, J=6.9 Hz), 4.12(2H, q, J=7.3 Hz), 4.66(2H, s); 5.41(1H, s), 7.09–7.29(7H, m), 7.34(1H, s), 7.36(1H, s), 7.48(1H,s)

Example 67

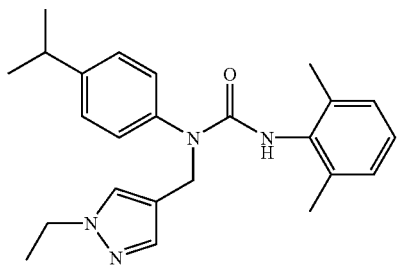

By the reaction and treatment in the same manner as in Example 1 using (1-ethylpyrazol-4-ylmethyl)(4-isopropylphenyl)amine (365 mg) and 2,6-dimethylisocyanate (221 mg) as starting materials, N'-(2,6-dimethylphenyl)-N-(1-ethylpyrazol-4-ylmethyl)-N-(4-isopropylphenyl)urea (510 mg) was obtained. melting point: 107.6° C.

$^1$H-NMR(CDCl$_3$)δ: 1.26(6H, d, J=6.9 Hz), 1.45(3H, t, J=7.3 Hz), 2.18(6H, s), 2.93(1H, sept, J=6.9 Hz), 4.13(2H, q, J=7.3 Hz), 4.69(2H, s), 5.49(1H, s), 7.01(3H, s), 7.15(2H, d, J=8.4 Hz), 7.27(2H, d, J=8.4 Hz), 7.34(1H, s), 7.44(1H, s)

Example 68

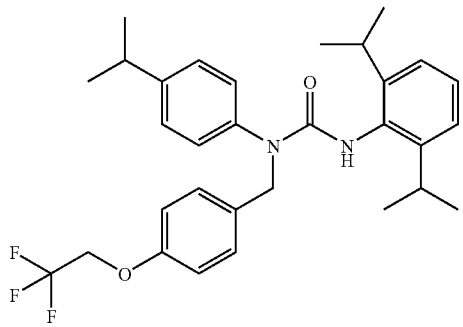

To a solution of (4-isopropylphenyl){(4-(2,2,2-trifluoroethoxy)phenyl)methyl}amine (1.12 g) in toluene (15 mL) was added 2,6-diisopropylphenyl isocyanate (1.1 mL), and the mixture was stirred at overnight room temperature. The reaction mixture was washed with saturated brine, dried over magnesium sulfate, and evaporated under reduced pressure. The residue was purified by silica gel column chromatography. The obtained crystals were subjected to recrystallization from diisopropyl ether to give N'-(2,6-diisopropylphenyl)-N-(4-isopropylphenyl)-N-{(4-(2,2,2-trifluoroethoxy)phenyl)methyl}urea (0.54 g). melting point: 138° C.

Formulation Example 1

Tablets containing the following ingredients were produced by a conventional method.

| ingredients | per tablet |
| --- | --- |
| compound of Example 1 | 10 mg |
| lactose | 125 mg |
| corn starch | 75 mg |
| talc | 4 mg |
| magnesium stearate | 1 mg |
| total weight | 215 mg |

Formulation Example 2

Capsules containing the following ingredients were produced by a conventional method.

| ingredients | per capsule |
| --- | --- |
| compound of Example 1 | 10 mg |
| lactose | 165 mg |
| corn starch | 20 mg |
| talc | 5 mg |
| weight of a capsule | 200 mg |

Formulation Example 3

Ointment containing the following ingredients was produced by a conventional method.

| ingredients | dose |
| --- | --- |
| compound of Example 1 | 0.2 g |
| white petrolatum | 97.8 g |
| liquid paraffin | 2 g |
| total weight | 100 g |

Formulation Example 4

Injection containing the following ingredients was produced by a conventional method.

| ingredients | dose |
| --- | --- |
| compound of Example 1 | 0.2 g |
| sodium chloride | 0.9 g |
| distilled water for injection | suitable amount |
| total weight | 100 g |

Formulation Example 5

Eye drop containing the following ingredients was produced by a conventional method.

| ingredients | |
| --- | --- |
| compound of Example 1 | 0.1 g |
| sodium chloride | 0.3 g |
| sterile purified water | suitable amount |
| total weight | 100 g |

The superior pharmacological effect of the compound of the formula (1) is verified by a series of the following tests.

Test Example 1

C5a Receptor Binding Assay

The C5a receptor binding inhibitory action of C5a and the test compound was evaluated by a receptor binding assay comprising reacting human cell line U-937 (human histiocytic lymphoma line), which expresses the C5a receptor, with [$^{125}$I]-human C5a (Amersham Pharmacia Biotech) in a MultiScreen (MILLIPORE). First, U-937 cell was stimulated with 1 mM dibutyryl cyclic AMP (dcAMP, SIGMA) for 2 days to express the C5a receptor (dcAMP-U-937 cell), and suspended in a binding buffer [50 mM HEPES, 1 mM CaCl$_2$, 5 mM MgCl$_2$, 0.5% bovine serum albumin (BSA, SIGMA), 0.02% NaN$_3$ (pH 7.2)] and stored at −80° C. The binding assay was started by the addition of 50 μL of dcAMP-U-937 cell suspension dissolved immediately before use, 25 μL of a binding buffer or a test compound solution, and 25 μL of [$^{125}$I]-C5a solution (final concentration 200 pM), to each well of the MultiScreen. For calculation of non-specific binding, a non-labeled C5a (final concentration 20 nM) was added instead of the test compound solution. After incubation at 4° C. for 2 hr, suction filtration and addition of 300 μL of the binding buffer were repeated 4 times to remove non-binding portion. After drying the MultiScreen, the radioactivity on the filter was measured using a gamma counter. The rate (% inhibition) of inhibition of C5a binding by the test compound was calculated by the following formula using the count value obtained without addition of the test compound as Total, the count value obtained with addition of non-labeled C5a as Non, and the count value obtained with addition of the test compound as Test.

% Inhibition=100−[(Test−Non)/(Total−Non)]×100

Further, the concentration ($IC_{50}$ value) of the test compound, at which binding of [$^{125}$I]-human C5a is inhibited by 50%, was calculated by two-interpolation method. In this evaluation system, $IC_{50}$ value of the compound of Example 34 was 100 nmol/L.

Test Example 2

Action on Increase of Intracellular $Ca^{2+}$ Concentration of C5a Stimulated Neutrophile A neutrophile fraction was separately taken from human peripheral venous blood using Lympholyte-poly (Cedarlane), and suspended in Hank's Balanced Salt Solution (HBSS, GIBCO BRL) supplemented with 1% fetal bovine serum (FBS). Then, Fura 2-AM (final concentration 5 μM, DOJINDO) was added to the neutrophile fraction ($5 \times 10^6$ cells/mL), and the mixture was incubated at 37° C. for 40 min. The cells were washed by centrifugation and suspended to the concentration of $1 \times 10^6$ cells/mL. The intracellular $Ca^{2+}$ concentration was measured using a spectrophotofluorometer (CAF-110, JASCO Corporation), and calculated from the ratio (Ex340 value/Ex380 value) of fluorescent intensities at 500 nm upon excitation at 340 nm and 380 nm, the former being Ex340 value, the latter being Ex380 value. To be specific, a neutrophile suspension (450 μL, $1 \times 10^6$ cells/mL) was dispensed to a cuvette having a stirrer bar at 5 min before the measurement and the suspension was heated to 37° C. Then the cuvette was set on CAF-110 set for 37° C., and the measurement was started. Immediately thereafter, 50 μL of a test compound solution was added. About 45 sec later, 5 μL of recombinant human C5a (final concentration 100 pmol/L) was added and the measurement was continued for about 1 min. Then, Triton X-100 (final concentration 0.2%) was added and the cells were dissolved, and, sb2 value, which was the Ex 340 value then, and Rmax value, which was the Ex340 value/Ex380 value then, was measured. Then, EGTA (final concentration 3 mmol/L) was added and sf2 value, which was the Ex340 value then, and Rmin value, which was the Ex340/Ex380 value then, was measured. From these measurement results, the intracellular $Ca^{2+}$ concentration was calculated from the following formula.

$$\text{Intracellular } Ca^{2+} \text{ concentration (nmol/L)} = \frac{(Ex340 \text{ value}/Ex380 \text{ value}) - R\text{min value}}{R\text{max value} - (Ex340 \text{ value}/Ex380 \text{ value})} \times 224 \times (sf2/sb2)$$

The rate (% inhibition) of the inhibition of increase in intracellular $Ca^{2+}$ concentration of C5a stimulated neutrophile by the test compound was calculated by the following formula, wherein the peak value of increase in intracellular $Ca^{2+}$ concentration derived by C5a without addition of the test compound is Max, the peak value of intracellular $Ca^{2+}$ concentration without addition of the test compound and without stimulation with C5a is Min, and the peak value of increase in intracellular $Ca^{2+}$ concentration derived by C5a with the addition of the test compound is Test.

% inhibition=100−[(Test−Min)/(Max−Min)]×100

Further, the concentration ($IC_{50}$ value) of the test compound, at which increase in intracellular $Ca^{2+}$ concentration of C5a-stimulated neutrophile is inhibited by 50%, was calculated by two-interpolation method.

The $IC_{50}$ value of the compound of Example 34 was 5 nmol/L. Moreover, addition of the compound of Example 34 (10 μmol/L) did not induce an increase in intracellular $Ca^{2+}$ and the agonistic action was not found.

Test Example 3

Action of C5a-Stimulated Neutrophile on Production of Reactive Oxygen Species

A neutrophile fraction was separately taken from human peripheral venous blood using Lympholyte-poly (Cedarlane), and suspended in Hank's Balanced Salt Solution (HBSS, GIBCO BRL) containing 1% fetal bovine serum (FBS) and 1 mmol/L of luminol (Wako Pure Chemical Industries, Ltd.). Reactive oxygen species was measured using a luminometer (MicroLumat, Berthold) for 96 well plate. That is, $1 \times 10^5$ cells/150 μL of neutrophile suspension and 25 μL of a test compound solution were added to a well, which was set in a MicroLumat set for 37° C. and stood for about 5 min. Then, 25 μL of C5a (final concentration 3 nmol/L) was added and luminescence produced by the reaction of the luminol and the reactive oxygen species was measured with the lapse of time for 15 min. The rate (% inhibition) of inhibition of the production of reactive oxygen species in C5a stimulated neutrophile by the test compound was calculated by the following formula, wherein the peak value of the production of reactive oxygen species derived by C5a without addition of the test compound is Max, the peak value of the production of reactive oxygen species without addition of the test compound and without C5a stimulation is Min, and the peak value of the production of reactive oxygen species derived by C5a with the addition of the test compound is Test.

% inhibition=100−[(Test−Min)/(Max−Min)]×100

In addition, the concentration ($IC_{50}$ value) of the test compound, at which the production of reactive oxygen species in C5a stimulated neutrophile is inhibited by 50%, was calculated by two-interpolation method.

The $IC_{50}$ value of the compound of Example 34 was 10 nmol/L.

Test Example 4

Action on Migrating Ability of C5a-Stimulated Neutrophile

A neutrophile fraction was separately taken from human peripheral venous blood using Lympholyte-poly (Cedarlane) and suspended in RPMI 1640 medium (GIBCO BRL) supplemented with 0.1% bovine serum albumin (BSA). To this neutrophile fraction ($5 \times 10^6$ cells/mL) was added Calcein-AM (final concentration 5 μM, FUNAKOSHI), and the mixture was incubated at 37° C. for 30 min. The cells were washed by centrifugation and suspended to a concentration of $1 \times 10^6$ cells/mL. The migration was evaluated by adding neutrophiles to chemotaxicell (pore size: 3 μm, KURABO) and measuring the neutrophiles that migrated outside the chemotaxicell. First, 100 pmol/L of C5a solution was added to 24 well plate (500 μL/well) and chemotaxicell was set in the well. Then, neutrophile suspension and test compound solution (200 μL each) were added to the inside of the chemotaxicell and incubated at 37° C., 5% $CO_2$ for 90 min. After the completion of the reaction, chemotaxicell was removed after shaking well and 100 μL of cell lysate solution (10% SDS, 0.01 mol/L HCl) was added. The fluorescent intensity of each well was measured by Cyto Fluor II (Ex: 485, Em: 530). The rate (% inhibition) of the inhibition of migration of C5a-stimulated neutrophile by the test compound was calculated by the following formula, wherein the fluorescence intensity of neutrophile that migrated by C5a stimulation without addition of the test compound is Max, the fluorescent intensity of neutrophile that migrated without addition of test compound and without C5a stimulation is Min, and the fluorescent intensity of neutrophile that migrated by C5a stimulation with the addition of the test compound is Test.

% inhibition=100−[(Test−Min)/(Max−Min)]×100

Further, the concentration ($IC_{50}$ value) of the test compound, at which migration of C5a-stimulated neutrophile is inhibited by 50%, was calculated by two-interpolation method.

The $IC_{50}$ value of the compound of Example 34 was 100 nmol/L.

Test Example 5

Action on C5a-Induced Decrease in Neutrophile in Cynomolgus Monkey

The action of the test compound on the decrease of neutrophile in peripheral blood, that occurs temporarily upon intravenous administration of human C5a to cynomolgus monkey, was evaluated. That is, the test compound was orally administered to cynomolgus monkey, and 4 hr later, human C5a was administered. The neutrophiles in peripheral blood were counted 2 min before and 1 min after administration of human C5a, and the rate (%) of decrease in neutrophiles in peripheral blood was calculated by the following formula. decrease rate (%)=100−[(neutrophiles in peripheral blood 1 min after administration of human C5a)/ (neutrophiles in peripheral blood 2 min before administration of human C5a)]×100

Using the following formula, moreover, the inhibition rate (% inhibition) of decrease in neutrophiles in peripheral blood by the test compound was calculated.

% inhibition=100−[(Test−Min)/(Max−Min)]×100

Test: decrease rate of neutrophiles in peripheral blood when test compound and human C5a were administered
Min: decrease rate of neutrophiles in peripheral blood upon administration of administration medium for test compound and administration medium for human C5a
Max: decrease rate of neutrophiles in peripheral blood upon administration of administration medium for test compound and human C5a In this evaluation system, the compound of Example 53 showed 74% inhibition at the dose of 30 mg/kg.

Test Example 6

Action on Collagen-Induced Arthritis in Monkey

Type II collagen derived from bovine (Collagen Research Center) is intradermally inoculated twice to the back of cynomolgus monkey, together with complete Freund's adjuvant H37Rv (Wako Pure Chemical Industries, Ltd.) on the first day of testing and day 21. The test compound is orally administered from day 22 to day 33 after inoculation. The swelling of four limb joints is observed according to the scores of 0 (no change)—3 (edema of 5 toes). The joint swelling score of each monkey is shown by the total scores of four limbs.

Test Example 7

Toxicity Test

In a single administration toxicity test, the test compound is administered to male and female SD rats (3 per group) and cynomolgus monkey (1 per group) and the toxicity by single administration is evaluated using the presence or absence of death incident, general condition and body weight as indices. In a repeat administration toxicity test, the test compound is repeatedly administered to male and female SD rats (6 per group) and male and female cynomolgus monkeys (2 per group) for 2 weeks and the toxicity of the test compound by repeat administration is evaluated using general condition, body weight, diet intake, hematological test, biochemical test for blood, weight of organs and autopsy (including pathological test of tissues) as indices.

Test Example 8

Evaluation of Bioavailability in Rat

The test compound is intravenously and orally administered to male SD rats (5 per group), and the blood is drawn with the lapse of time. Using high performance liquid chromatography, the drug concentration in plasma is measured. The bioavailability (BA) is calculated by the following formula.

$$\frac{AUC \text{ by oral administration}}{AUC \text{ by intravenous administration}} \times \frac{\text{dose of intravenous administration}}{\text{dose of oral administration}} \times 100 (\%)$$

AUC: plasma concentration−area under time curve

INDUSTRIAL APPLICABILITY

The compound of the present invention has a C5a receptor antagonistic action and is useful as an agent for the prophylaxis or treatment of diseases or syndromes due to inflammation caused by C5a [e.g., autoimmune diseases such as rheumatism, systemic lupus erythematosus and the like, sepsis, adult respiratory distress syndrome, chronic obstructive pulmonary disease, allergic diseases such as asthma and the like, atherosclerosis, cardiac infarction, brain infarction, psoriasis, Alzheimer's disease and serious organ injury (e.g., pneumonia, nephritis, hepatitis and pancreatitis and the like) due to activation of leukocytes caused by ischemia, trauma, burn, surgical invasion and the like]. In addition, it is useful as an agent for the prophylaxis or treatment of infectious diseases caused by bacteria or virus that invades via a C5a receptor.

This application is based on a patent application No. 243290/2000 filed in Japan, the contents of which are all hereby incorporated by reference.

What is claimed is:
1. A urea derivative of the formula (1)

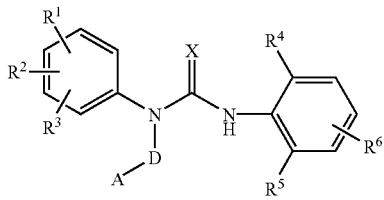

wherein
R¹, R² and R³ are the same or different and each is hydrogen, alkyl optionally having a substituent, cycloalkyl optionally having a substituent, alkenyl optionally having a substituent, alkynyl optionally having a substituent, hydroxy, alkoxy optionally having a substituent, mercapto, alkylthio optionally having a substituent, halogen, nitro, nitrile, amino, alkylamino, cyclic amino, alkylsulfonyl, carbamoyl, acylamino, sulfamoyl, acyl, carboxy, alkoxycarbonyl, aryl optionally having a substituent or heteroaryl optionally having a substituent,
D is a bond or alkylene optionally having a substituent,
A is alkyl optionally having a substituent, cycloalkyl optionally having a substituent, aryl optionally having a substituent or heteroaryl optionally having a substituent,
R⁴ and R⁵ are the same or different and each is alkyl optionally having a substituent, alkoxy optionally having a substituent, hydroxy or halogen,
R⁶ is hydrogen, alkyl optionally having a substituent, alkoxy optionally having a substituent, hydroxy or halogen, and
X is oxygen atom or sulfur atom,
or a pharmaceutically acceptable salt thereof,
wherein the urea derivative is a non-heterocyclic.

2. The urea derivative of claim 1, wherein D of the formula (1) is alkylene optionally having a substituent and A is aryl optionally having a substituent or heteroaryl optionally having a substituent, or a pharmaceutically acceptable salt thereof.

3. The urea derivative of claim 1, wherein R¹, R² and R³ of the formula (1) are the same or different and each is hydrogen or alkyl having 2 to 4 carbon atoms, or a pharmaceutically acceptable salt thereof.

4. The urea derivative of claim 1, wherein R⁴ and R⁵ of the formula (1) are the same or different and each is alkyl, alkoxy or halogen, or a pharmaceutically acceptable salt thereof.

5. The urea derivative of claim 1, which is a compound selected from the group consisting of
N-benzyl-N'-(2,6-dimethylphenyl)-N-(4-octylphenyl)urea,
N'-(2,6-diisopropylphenyl)-N-[(4-methoxyphenyl)methyl]-N-(4-octylphenyl)urea,
N'-(2,6-diisopropylphenyl)-N-[(4-dimethylaminophenyl)methyl]-N-(4-octylphenyl)urea,
N-(4-butylphenyl)-N'-(2,6-diisopropylphenyl)-N-[(4-dimethylaminophenyl)methyl]urea,
N'-(2,6-diisopropylphenyl)-N-[(4-dimethylaminophenyl)methyl]-N-(4-methoxyphenyl)urea,
N'-(2,6-diisopropylphenyl)-N-[(4-dimethylaminophenyl)methyl]-N-(4-ethylphenyl)urea,
N'-(2,6-diisopropylphenyl)-N-[(4-dimethylaminophenyl)methyl]-N-(4-propylphenyl)urea,
N'-(2,6-diisopropylphenyl)-N-[(4-dimethylaminophenyl)methyl]-N-(4-isopropylphenyl)urea,
N'-(2,6-diisopropylphenyl)-N-[(4-dimethylaminophenyl)methyl]-N-(4-ethoxyphenyl)urea,
N'-(2,6-diisopropylphenyl)-N-(4-isopropylphenyl)-N-[(4-isopropylphenyl)methyl]urea,
N-butyl-N'-(2,6-diisopropylphenyl)-N-(4-isopropylphenyl)urea,
N-(3,4-dichlorophenylmethyl)-N'-(2,6-diisopropylphenyl)-N-(4-isopropylphenyl)urea,
N'-(2,6-diisopropylphenyl)-N-[(2,4-dimethoxyphenyl)methyl]-N-(4-isopropylphenyl)urea,
N'-(2,6-diisopropylphenyl)-N-[(4-dimethylaminophenyl)methyl]-N-(2,4-dimethylphenyl)urea,
N'-(2,6-diisopropylphenyl)-N-[(2,4-dimethylphenyl)methyl]-N-(4-isopropylphenyl)urea,
N'-(2,6-diisopropylphenyl)-N-[(4-fluorophenyl)methyl]-N-(4-isopropylphenyl)urea,
N-[(4-chlorophenyl)methyl]-N'-(2,6-diisopropylphenyl)-N-(4-isopropylphenyl)urea,
N-[(4-bromophenyl)methyl]-N'-(2,6-diisopropylphenyl)-N-(4-isopropylphenyl)urea,
N'-(2,6-diisopropylphenyl)-N-(4-isopropylphenyl)-N-[(4-trifluoromethylphenyl)methyl]urea,
N-[(2,4-dichlorophenyl)methyl]-N'-(2,6-diisopropylphenyl)-N-(4-isopropylphenyl)urea,
N'-(2,6-diisopropylphenyl)-N-[(4-hydroxyphenyl)methyl]-N-(4-isopropylphenyl)urea and
N'-(2,6-diisopropylphenyl)-N-(4-isopropylphenyl)-N-[(4-methylthiophenyl)methyl]urea,
or a pharmaceutically acceptable salt thereof.

6. A pharmaceutical composition comprising the urea derivative of claim 1 or a pharmaceutically acceptable salt thereof, and a pharmaceutically acceptable additive.

7. A therapeutic drug for a disease, in which C5a is involved, which comprises the urea derivative of claim 1 or a pharmaceutically acceptable salt thereof as an active ingredient.

8. The therapeutic drug of claim 7, wherein the disease, in which C5a is involved, is an autoimmune disease, sepsis, adult respiratory distress syndrome, chronic obstructive pulmonary disease, an allergic disease, atherosclerosis, cardiac infarction, brain infarction, psoriasis, Alzheimer's disease, ischemia, trauma, burn or serious organ injury.

9. A C5a receptor antagonist comprising the urea derivative of claim 1 or a pharmaceutically acceptable salt thereof as an active ingredient.

10. The C5a receptor antagonist of claim 9, which is a therapeutic drug of an infectious disease caused by bacteria or virus that invades via the C5a receptor.

11. The C5a receptor antagonist of claim 9, which is used in combination with an agent for the treatment of an autoimmune disease, sepsis, adult respiratory distress syndrome, chronic obstructive pulmonary disease, an allergic disease, atherosclerosis, cardiac infarction, brain infarction, psoriasis, Alzheizner's disease, ischemia, trauma, burn or serious organ injury.

12. A combination drug with an agent for the treatment of an autoimmune disease, sepsis, adult respiratory distress syndrome, chronic obstructive pulmonary disease, an allergic disease, atherosclerosis, cardiac infarction, brain infarction, psoriasis, Alzheimer's disease, ischemia, trauma, burn or serious organ injury, which comprises the urea derivative of claim 1 or a pharmaceutically acceptable salt thereof as an active ingredient.

13. A method for the treatment of a disease, in which C5a is involved, which comprises administrating an effective amount of the urea derivative of claim 1 or a pharmaceutically acceptable salt thereof to a subject.

14. The method for the treatment of claim 13, wherein the disease, in which C5a is involved, is an autoimmune disease, sepsis, adult respiratory distress syndrome, chronic obstructive pulmonary disease, an allergic disease, atherosclerosis, cardiac infarction, brain infarction, psoriasis, Alzheimer's disease, ischemia, trauma, burn or serious organ injury.

* * * * *